United States Patent
Schlenoff et al.

(10) Patent No.: US 7,722,752 B2
(45) Date of Patent: May 25, 2010

(54) VARIABLE CHARGE FILMS FOR CONTROLLING MICROFLUIDIC FLOW

(75) Inventors: Joseph B. Schlenoff, Tallahassee, FL (US); Zhijie Sui, Tucson, AZ (US)

(73) Assignee: Florida State University Research Foundation, Tallahassee, FL (US)

( * ) Notice: Subject to any disclaimer, the term of this patent is extended or adjusted under 35 U.S.C. 154(b) by 1484 days.

(21) Appl. No.: 11/070,770

(22) Filed: Mar. 2, 2005

(65) Prior Publication Data

US 2006/0065529 A1    Mar. 30, 2006

Related U.S. Application Data

(60) Provisional application No. 60/549,341, filed on Mar. 2, 2004.

(51) Int. Cl.
  *G01N 27/447*  (2006.01)
  *G01N 27/453*  (2006.01)
  *B01D 57/02*   (2006.01)
(52) U.S. Cl. .................. 204/600; 204/450; 204/622; 204/454; 204/471; 204/451; 205/775; 205/791
(58) Field of Classification Search .............. 204/450, 204/451, 454, 461, 471, 600, 622; 428/515; 427/337, 115; 205/775, 785.5, 776.5, 789, 205/791
See application file for complete search history.

(56) References Cited

U.S. PATENT DOCUMENTS

| 3,467,604 A | 9/1969 | Michaels |
| 4,168,112 A | 9/1979 | Ellis et al. |
| 4,169,023 A | 9/1979 | Sata et al. |
| 4,501,835 A | 2/1985 | Berke |
| 4,654,235 A | 3/1987 | Effenberger et al. |
| 4,673,566 A | 6/1987 | Goosen et al. |

(Continued)

FOREIGN PATENT DOCUMENTS

WO    WO 02/085500 A1 * 10/2002

OTHER PUBLICATIONS

Beebe et al., Microfluidic Technology for Assisted Reproduction, 2002, Elsevier Science Inc., Theriogenology 57:125-135.*

(Continued)

*Primary Examiner*—Nam X Nguyen
*Assistant Examiner*—Jennifer Dieterle
(74) *Attorney, Agent, or Firm*—Senniger Powers LLP

(57) ABSTRACT

A microfluidic device for carrying a liquid, the device comprising a microfluidic channel having an interior wall and a polyelectrolyte film on the interior wall whereby liquid carried by the channel contacts the polyelectrolyte film, the polyelectrolyte film having a thickness of about 1 to about 1000 nanometers and comprising an interpenetrating network of a predominantly positively charged polymer and a predominantly negatively charged polymer, the predominantly positively charged polymer, the predominantly negatively charged polymer or both containing (i) a pH insensitive positively or negatively charged repeat unit having a pKa greater than 9 or less than 3, and (ii) a pH sensitive repeat unit, the pH sensitive repeat unit having a pKa of 3 to 9, whereby the pH of liquid in the microfluidic channel may be used to control the velocity or direction of electroosmotic flow of the liquid within said microfluidic channel.

27 Claims, 12 Drawing Sheets

U.S. PATENT DOCUMENTS

| | | | | |
|---|---|---|---|---|
| 4,936,974 | A | | 6/1990 | Rose et al. |
| 4,997,537 | A | * | 3/1991 | Karger et al. ............... 204/453 |
| 5,098,539 | A | * | 3/1992 | Shieh ......................... 204/453 |
| 5,208,111 | A | | 5/1993 | Decher et al. |
| 5,370,777 | A | * | 12/1994 | Guttman et al. ............. 204/452 |
| 5,711,915 | A | | 1/1998 | Siegmund et al. |
| 5,807,636 | A | | 9/1998 | Sheu et al. |
| 6,402,918 | B1 | | 6/2002 | Schlenoff et al. |
| 6,451,871 | B1 | | 9/2002 | Winterton et al. |
| 6,468,657 | B1 | | 10/2002 | Hou et al. |
| 6,586,065 | B1 | | 7/2003 | Katayama et al. |
| 6,610,789 | B2 | | 8/2003 | Watakabe et al. |
| 6,660,367 | B1 | * | 12/2003 | Yang et al. .................. 428/188 |
| 6,841,054 | B2 | | 1/2005 | Schlenoff et al. |
| 6,860,980 | B2 | | 3/2005 | Locascio et al. |
| 2002/0053514 | A1 | | 5/2002 | Locascio et al. |
| 2002/0117517 | A1 | * | 8/2002 | Unger et al. ................ 222/214 |
| 2002/0130045 | A1 | | 9/2002 | Schlenoff et al. |
| 2003/0124368 | A1 | * | 7/2003 | Lynn et al. .................. 428/483 |
| 2003/0219384 | A1 | | 11/2003 | Donath et al. |
| 2003/0230490 | A1 | * | 12/2003 | Swedberg et al. ........... 204/471 |
| 2004/0022691 | A1 | | 2/2004 | Allen et al. |
| 2004/0044100 | A1 | | 3/2004 | Schlenoff et al. |
| 2004/0060481 | A1 | | 4/2004 | Schlenoff |
| 2004/0084312 | A1 | * | 5/2004 | Warner et al. ............... 204/454 |
| 2004/0149572 | A1 | | 8/2004 | Schlenoff et al. |
| 2004/0265603 | A1 | | 12/2004 | Schlenoff |
| 2005/0025675 | A1 | | 2/2005 | Schlenoff et al. |

OTHER PUBLICATIONS

Lixin Shi et al., Site-selective lateral multilayer assembly of bienzyme with polyelectrolyte on ITO electrode based on electric field-induced directly layer-by-layer deposition, 2003, American Chemical Society, Biomacromolecules, vol. 4, No. 5, pp. 1161-1167.*
Kapnissi et al. (Analytical Separations Using Molecular Micelles in Op n-Tubular Capillary Electrochromatography, Anal. Chem. 2002, 74, 2328-2335).*
Hayes et al. (Effects of buffer pH on electroosmotic flow control by an applied radial voltage for capillary zone electrophoresis, Anal. Chem., 1993, 65 (1), pp. 27-31).*
Yoo et al. (Controlling Bilayer Composition and Surface Wettability of Sequentially Adsorbed Multilayers of Weak Polyelectrolytes, Macromolecules, 1998, 31, pp. 4309-4318).*
Decher et al. (Multilayer Thin Films, Wiley-VCH Verlag GmbH & Co. KGaA, 2002, pp. 1-46).*
Fu et al. (The morphological study of chemically crosslinked polymer gel electrolyte, Journal of Matl. Science, 2002, 13, 491-495).*
Cheng, Y., et al., "Ultrathin Polypeptide Multilayer Films for the Fabrication of Model Liquid/Liquid Electrochemical Interfaces," J. Phys. Chem. B 1999, pp. 8726-8731, vol. 103, No. 41, Published Sep. 18, 1999.
Barker, S.L.R., et al., "Control of Flow Direction in Microfluidic Devices with Polyelectrolyte Multilayers," Analytical Chemistry, Dec. 15, 2000, pp. 5925-5929, vol. 72, No. 24.
Caruso, F., et al., "Assembly of Alternating Polyelectrolyte and Protein Multilayer Films for Immunosensing," Langmuir, 1997, pp. 3427-3433, vol. 13, No. 13.
Chen, W., et al., "Layer-by-Layer Deposition: A Tool for Polymer Surface Modification," Macromolecules, 1997, pp. 78-86, vol. 30, No. 1.
Chluba, J., et al., "Peptide Hormone Covalently Bound to Polyelectrolytes and Embedded into Multilayer Architectures Conserving Full Biological Activity," Biomacromolecules, 2001, pp. 800-805, vol. 2, No. 3.
Dai, J., et al., "Controlling the Permeability of Multilayered Polyelectrolyte Films Through Derivatization, Cross-Linking, and Hydrolysis," Langmuir, 2001, pp. 931-937, vol. 17, No. 3.
Decher, G., "Fuzzy Nanoassemblies: Toward Layered Polymeric Multicomposites," Science, Aug. 29, 1997, pp. 1232-1237, vol. 277.
Decher, G., "Polyelectrolyte Multilayers, An Overview," Multilayer Thin Films, 2002, pp. 1-46.
Dubas, S.T., et al., "Multiple Membranes From "True" Polyelectrolyte Multilayers," Journal of the American Chemical Society, May 10, 2001, pp. 5368-5369, vol. 123, No. 22, American Chemical Society.
Dubas, S.T., et al., "Swelling and Smoothing of Polyelectrolyte Multilayers by Salt," Langmuir, 2001, pp. 7725-7727, vol. 17, No. 25.
Fou, A.C., et al., "Fabrication and Properties of Light-Emitting Diodes Based on Self-Assembled Multilayers of Poly(phenylene vinylene)," J. Appl. Phys., May 15, 1996, pp. 7501-7509, vol. 79, No. 10.
Graul, T.W., et al., "Capillaries Modified by Polyelectrolyte Multilayers for Electrophoretic Separations," Analytical Chemistry, Sep. 15, 1999, pp. 4007-4013, vol. 71, No. 18.
Hammond, P.T., et al., "Formation of Polymer Microstructures by Selective Deposition of Polyion Multilayers Using Patterned Self-Assembled Monolayers as a Template," Macromolecules, 1995, pp. 7569-7571, vol. 28, No. 22.
Harris, J.J., et al., "Electrochemical and in Situ Ellipsometric Investigation of the Permeability and Stability of Layered Polyelectrolyte Films," Langmuir, 2000, pp. 2006-2013, vol. 16, No. 4.
Harris, J.J., et al., "Layered Polyelectrolyte Films as Selective, Ultrathin Barriers for Anion Transport," Chem. Mater., 2000, pp. 1941-1946, vol. 12, No. 7.
Harris, J.J., et al., "Synthesis of Passivating, Nylon-Like Coatings Through Cross-Linking of Ultrathin Polyelectrolyte Films," Journal of the American Chemical Society, 1999, pp. 1978-1979, vol. 121, No. 9, American Chemical Society.
Holmlin, R.E., et al., "Zwitterionic SAMs that Resist Nonspecific Absorption of Protein from Aqueous Buffer," Langmuir, 2001, pp. 2841-2850, vol. 17, No. 9.
Hoogeveen, N.G., et al., "Formation and Stability of Multilayers of Polyelectrolytes," Langmuir, 1996, pp. 3675-3681, vol. 12, No. 15.
Hsieh, M.C., et al., "Surface "Priming" for Layer-by-Layer Deposition: Polyelectrolyte Multilayer Formation on Allylamine Plasma-Modified Poly(tetrafluoroethylene)," Macromolecules, 1997, pp. 8453-8458, vol. 30, No. 26.
Huck, W.T.S., et al., "Patterned Polymer Multilayers as Etch Resists," Langmuir, 1999, pp. 6862-6867, vol. 15, No. 20.
Ichinose, I., et al., "Electrostatic Absorption of Cytochrome $c$ on Ultrathin $ZrO_2$-Gel Layers and Preparation of Alternate Multilayers," Langmuir, 2003, pp. 3883-3888, vol. 19, No. 9.
Jiang, X., et al., "Selective Deposition in Layer-by-Layer Assembly: Functional Graft Copolymers as Molecular Templates," Langmuir, 2000, pp. 8501-8509, vol. 16, No. 22.
Jorgenson, J.W., et al., "Zone Electrophoresis in Open-Tubular Glass Capillaries," Analytical Chemistry, Jul. 1981, pp. 1298-1302, vol. 53, No. 8.
Kapnissi, C.P., et al., "Analytical Separations Using Molecular Micelles in Open-Tubular Capillary Electrochromatography," Analytical Chemistry, May 15, 2002, pp. 2328-2335, vol. 74, No. 10.
Kozlovskaya, V. et al., "Hydrogen-Bonded Polymer Capsules Formed by Layer-by-Layer Self-Assembly," Macromolecules, 2003, pp. 8590-8592, vol. 36, No. 23.
Krasemann, L., et al., "Selective Ion Transport Across Self-Assembled Alternating Multilayers of Cationic and Anionic Polyelectrolytes," Langmuir, 2000, pp. 287-290, vol. 16, No. 2.
Ladam, G., et al., "Protein Absorption onto Auto-Assembled Polyelectrolyte Films," Langmuir, 2001, pp. 878-882, vol. 17, No. 3.
Ladam, G., et al., "Protein Interactions with Polyelectrolyte Multilayers: Interactions Between Human Serum Albumin and Polystyrene Sulfonate/Polyallylamine Multilayers," Biomacromolecules, 2000, pp. 674-687, vol. 1, No. 4.
Lvov, Y., et al., "Assembly of Multicomponent Protein Films by Means of Electrostatic Layer-by-Layer Absorption," Journal of the American Chemical Society, 1995, pp. 6117-6123, vol. 117, No. 22, American Chemical Society.
Lvov, Y., et al., "Biocolloids with Ordered Urease Multilayer Shells as Enzymatic Reactors," Analytical Chemistry, Sep. 1, 2001, pp. 4212-4217, vol. 73, No. 17.

Lvov, Y.M., et al., "Direct Electrochemistry of Myoglobin and Cytochrome P450$_{cam}$ in Alternate Layer-by-Layer Films with DNA and Other Polyions," *Journal of the American Chemical Society*, 1998, pp. 4073-4080, vol. 120, No. 17, American Chemical Society.

Mamedov, A.A., et al., "Free-Standing Layer-by-Layer Assembled Films of Magnetite Nanoparticles," *Langmuir*, 2000, pp. 5530-5533, vol. 16, No. 13.

Matthews, J.R., et al., "Surfaces Designed for Charge Reversal," *Journal of the American Chemical Society*, 2003, pp. 6428-6433, vol. 125, No. 21, American Chemical Society.

Mendelsohn, J.D., et al., "Fabrication of Microporous Thin Films from Polyelectrolyte Multilayers," *Langmuir*, 2000, pp. 5017-5023, vol. 16, No. 11.

Mendelsohn, J.D., et al., "Rational Design of Cytophilic and Cytophobic Polyelectrolyte Multilayer Thin Films," *Biomacromolecules*, 2003, pp. 96-106, vol. 4, No. 1.

Möhwald, H., et al., "Smart Capsules," *Multilayer Thin Films*, 2002, pp. 363-392.

Mrksich, M., et al., "Surface Plasmon Resonance Permits in Situ Measurement of Protein Absorption on Self-Assembled Monolayers of Alkanethiolates on Gold," *Langmuir*, 1995, pp. 4383-4385, vol. 11, No. 11.

Müller, M., et al., "Deposition and Properties of Polyelectrolyte Multilayers Studied by ATR-FTIR Spectroscopy," *Materials Science and Engineering*, 1999, pp. 163-169, C 8-9.

Müller, M., et al., "Polyelectrolyte Complex Layers: A Promising Concept for Anti-Fouling Coatings Verified by in-situ ATR-FTIR Spectroscopy," *Macromolecular Rapid Communications*, 1999, pp. 607-611, vol. 20.

Müller, M., et al., "Selective Interaction Between Proteins and the Outermost Surface of Polyelectrolyte Multilayers: Influence of the Polyanion Type, pH and Salt," *Macromolecular Rapid Communications*, 2001, pp. 390-395, vol. 22.

Onda, M., et al., "Sequential Actions of Glucose Oxidase and Peroxidase in Molecular Films Assembled by Layer-by-Layer Alternate Absorption," *Biotechnology and Bioengineering*, Jul. 20, 1996, pp. 163-167, vol. 51, No. 2.

Overberger, C.G., et al., "Imidazole-Containing Polymers. Synthesis and Polymerization of the Monomer 4(5)-Vinylimidazole," *Journal of the American Chemical Society*, Apr. 5, 1963, pp. 951-955, vol. 85, American Chemical Society.

Pei, R., et al., "Assembly of Alternating Polycation and DNA Multilayer Films by Electrostatic Layer-by-Layer Absorption," *Biomacromolecules*, 2001, pp. 463-468, vol. 2, No. 2.

Raposo, M., et al., "Absorption Mechanisms in Layer-by-Layer Films," 1998, 13 pages.

Richert, L., et al., "Layer by Layer Buildup of Polysaccharide Films: Physical Chemistry and Cellular Adhesion Aspects," *Langmuir*, 2004, pp. 448-458, vol. 20, No. 2.

Rmaile, H.H., et al., "Optically Active Polyelectrolyte Multilayers as Membranes for Chiral Separations," *Journal of the American Chemical Society*, 2003, pp. 6602-6603, vol. 125, No. 22, American Chemical Society.

Rosidian, A., et al., "Ionic Self-Assembly of Ultrahard $ZrO_2$/Polymer Nanocomposite Thin Films," *Advanced Materials*, 1998, pp. 1087-1091, vol. 10, No. 14.

Salloum, D.S., et al., "Protein Absorption Modalities on Polyelectrolyte Multilayers," *Biomacromolecules*, 2004, pp. 1089-1096, vol. 5, No. 3.

Schlenoff, J.B., et al., "Sprayed Polyelectrolyte Multilayers," *Langmuir*, 2000, pp. 9968-9969, vol. 16, No. 26.

Schwinté, P., et al., "Stabilizing Effects of Various Polyelectrolyte Multilayer Films on the Structure of Absorbed/Embedded Fibrinogen Molecules: An ATR-FTIR Study," *J. Phys. Chem. B*, 2001, pp. 11906-11916, vol. 105, No. 47.

Serizawa, T., et al., "Alternating Bioactivity of Polymeric Layer-by-Layer Assemblies: Anticoagulation vs Procoagulation of Human Blood," *Biomacromolecules*, 2002, pp. 724-731, vol. 3, No. 4.

Stepp, J., et al., "Electrochromism and Electrocatalysis in Viologen Polyelectrolyte Multilayers," *Journal of the Electrochemical Society*, Jun. 1997, pp. L155-L157, vol. 144, No. 6.

Stroeve, P., et al., "Gas Transfer in Supported Films Made by Molecular Self-Assembly of Ionic Polymers," *Thin Solid Films* 284-285, 1996, pp. 708-712.

Sui, Z., et al., "Controlling Electroosmotic Flow in Microchannels with pH-Responsive Polyelectrolyte Multilayers," *Langmuir*, 2003, pp. 7829-7831, vol. 19, No. 19.

Sukhishvili, S.A., et al., "Layered, Erasable Polymer Multilayers Formed by Hydrogen-Bonded Sequential Self-Assembly," *Macromolecules*, 2002, pp. 301-310, vol. 35, No. 1.

Szleifer, I., "Polymers and Proteins: Interactions at Interfaces," *Biomaterials*, 1997, pp. 337-344.

Thierry, B., et al., "Bioactive Coatings of Endovascular Stents Based on Polyelectrolyte Multilayers," *Biomacromolecules*, 2003, pp. 1564-1571, vol. 4, No. 6.

Tieke, B., et al., "Ultrathin Self-Assembled Polyelectrolyte Multilayer Membranes," *The European Physical Journal E*, 2001, pp. 29-39, vol. 5.

Yoo, D., et al., "Controlling Bilayer Composition and Surface Wettability of Sequentially Absorbed Multilayers of Weak Polyelectrolytes," *Macromolecules*, 1998, pp. 4309-4318, vol. 31, No. 13.

Zou, H., et al., "Monolithic Stationary Phases for Liquid Chromatography and Capillary Electrochromatography," *Journal of Chromatography A*, 2002, pp. 5-32, vol. 954.

\* cited by examiner

1 μm

1 μm

VARIABLE CHARGE FILMS FOR CONTROLLING MICROFLUIDIC FLOW

CROSS-REFERENCE TO RELATED APPLICATIONS

This application claims priority from U.S. provisional application Ser. No. 60/549,341, filed on Mar. 2, 2004.

STATEMENT REGARDING FEDERALLY SPONSORED RESEARCH

This invention was made with Government support under Grant DMR 9727717 awarded by the National Science Foundation. The Government has certain rights in this invention.

BACKGROUND OF THE INVENTION

The present invention relates to the field of microfluidics and, more particularly, to using polyelectrolyte complex films to control the magnitude and direction of electroosmotic fluid flow within microfluidic channels.

In the field of microfluidics, liquid is moved through passages of micrometers dimension. These passages may be isolated or interconnected, and may be part of a larger scheme for performing fluid manipulation for the purposes of analysis or synthesis, for example, in a lab-on-a-chip apparatus. Microfluidic flow may be employed for analytical separations, or for moving reagents and samples through different reaction and/or detection zones. Various means are available for causing liquid to flow in microfluidic systems. For example, flow may be caused by pressure differences between ends of a microfluidic channel. Alternatively, flow may be caused by electroosmosis. Electroosmotic flow, EOF, of liquid through a microfluidic passage requires a net immobile charge on the interior surface of said passage, in contact with the liquid. The immobile surface charge is balanced by mobile counterions of the opposite charge from the fluid, usually water. Depending on the sign of the surface charge, the microfluidic channel thus contains an excess of mobile cations or anions. Under the influence of an electric field, imposed along the microfluidic channel by electrodes (anode and cathode) in contact with the fluid, there is a net migration, towards one end of the microfluidic channel, of anions or cations. Since these ions are solvated, they drag solvent molecules with them, causing a net flow of solvent within the microfluidic channel. If the surface charge on the interior of the microfluidic channel is negative, the channel will comprise excess cations, and fluid flow will be towards the negative electrode (the "normal" direction). If the surface charge is positive, the microfluidic channel will comprise excess anions, and net flow will be towards the positive electrode (the "reversed" direction). Since the direction and velocity of EOF is critically dependent on both the sign and magnitude of the surface charge on the interior of the microfluidic channel, there is a need for a means to produce a well-defined, stable surface charge within microfluidic systems.

EOF is advantageous compared to pressure-driven flow because the flow profile in EOF is more plug-like, whereas the flow profile in pressure-driven flow is parabolic. A plug-like flow profile leads to less dispersion of material flowing through a microfluidic channel. In addition, EOF is simple to implement on a chip, requiring only the placement of electrodes.

Species to be transported within microfluidic channels by EOF are swept along by the movement of the liquid. If a species in a microfluidic channel is charged it also experiences a force due to the electric field imposed on the channel. Motion due to the charge of a species within a liquid or gel under an applied field is known as electrophoresis. A charged species within a microfluidic channel therefore experiences displacement due to EOF and electrophoretic flow simultaneously. The differential speed of migration between two or more charged species as they travel down a microfluidic channel permits these species to be separated from each other. In some cases, it is required that a charged species moves by electrophoresis only, and therefore the net charge on the microfluidic channel must be zero to completely suppress EOF.

Capillary zone electrophoresis, CZE, is one embodiment of a microfluidic channel where the channel is formed by a length of capillary tubing, typically fused silica, of internal diameter in the range 10 micrometers to 200 micrometers (see Rose and Jorgenson, U.S. Pat. No. 4,936,974). The length of the capillary is typically a few tens of centimeters and the exterior of the capillary is usually coated with a polymer, such as a polyimide, to impart physical durability. The capillary is filled with electrolyte, typically buffered aqueous solution, and the two ends are dipped into a reservoir. A voltage, typically in the kilovolts range, is applied along the length of the capillary by electrodes also dipping into the reservoir. The electric field, measured in volts per centimeter, is a critical parameter, so shorter lengths of capillary require lower applied voltage. What may be considered the first apparatus for CZE was described by Jorgenson and Lukas (see J. Jorgenson and K. D. Lukas, *Analytical Chemistry*, 53, 1298, (1981)).

Polyelectrolytes are macromolecules comprising a plurality of charged repeat units. Amorphous complexes may be formed by contacting solutions of polyelectrolytes bearing opposite charges. The driving force for association, or complexation, of polyelectrolytes is multiple ion pairing between oppositely charged repeat units on different molecules.

Recently, thin films of polyelectrolyte complexes have been prepared using polyelectrolytes which are alternately deposited on a substrate or substratum. See Decher and Schlenoff, Eds., *Multilayer Thin Films—Sequential Assembly of Nanocomposite Materials*, Wiley-VCH, Weinheim (2003); Decher, *Science*, 277, 1232 (1997). Decher and Hong (U.S. Pat. No. 5,208,111) disclose a method for a buildup of multilayers by alternating dipping, i.e., cycling a substrate between two reservoirs containing aqueous solutions of polyelectrolytes of opposite charge, with an optional rinse step in polymer-free solution following each immersion. Each cycle adds a layer of polymer via ion pairing forces to the oppositely-charged surface and reverses the surface charge thereby priming the film for the addition of the next layer. Films prepared in this manner tend to be uniform, follow the contours and irregularities of the substrate, and are typically between about 10 nm and about 10,000 nm thick. The thickness of a film depends on many factors, including the number of layers deposited, the ionic strength of the solutions, the types of polymers, the deposition time, the solution pH, the temperature, and the solvent used. Although studies have shown that the substantial interpenetration of the individual polymer layers results in little composition variation over the thickness of a film, such polymer thin films are, nevertheless, referred to as polyelectrolyte multilayers (PEMUs).

Though recently developed, PEMUs are being used in a wide variety of fields including light emitting devices, non-linear optics, sensors, enzyme active thin films, electrochromics, conductive coatings, patterning, anticorrosion coatings, antistatic coatings, lubricating films, biocompatibilization, dialysis, and as selective membranes for the separation of gaseous and dissolved ionic species. See Fou et al., *J. Appl. Phys.*, 79, 7501 (1996); Decher et al., *J. Biosens. Bioelect.* 9, 677 (1994); Sun et al., *Macromol. Chem. Phys.* 197, 147 (1996); Onda et al., *Biotech Bioeng.* 51, 163 (1996); Lvov et al., *J. Am. Chem. Soc.* 120, 40733 (1998); Laurent et al., *Langmuir* 13, 1552 (1997); Stepp et al., *J. Electrochem. Soc.* 144, L155 (1997); Cheung et al., *Thin Solid Films* 244, 985 (1994); Hammond et al., *Macromolecules* 28, 7569 (1995); Huck et al., *Langmuir* 15, 6862 (1999); Stroeve et al., *Thin Solid Films* 284, 708 (1996); Levasalmi et al., *Macromolecules* 30, 1752 (1997); Harris et al., *Langmuir* 16, 2006 (2000); Krasemann et al., *Langmuir* 16, 287 (2000); Harris et al., *J. Am. Chem. Soc.* 121, 1978 (1999); and Harris et al., *Chem. Mater.* 12, 1941 (2000).

Polyelectrolyte complexes are known to moderate interactions with biological systems, usually with the purpose of rendering an article or object inert to biological activity. That is, a coating of polyelectrolyte complex does not elicit undesirable inflammation or immune responses. Fine tuning of protein adsorption at the solid/liquid interface is critical in certain areas of materials science and biomedical engineering. Systems for delivery or biosensors, for example, bear modified surfaces designed to enhance or minimize protein adsorption. The latter goal is generally desirable for blood-contacting devices, chromatographic supports, contact lenses, and immunoassays, to name a few. Due to their ease of use and water compatibility, PEMUs have been investigated as surface-modifying agents for protein interactions (see Ladam, G.; Gergely, C.; Senger, B.; Decher, G.; Voegel, J. C.; Schaaf, P.; Cuisinier, F. J. G. *Biomacromolecules* 1, 674 (2000)). For example, polyelectrolyte complexes have been coated on Islets of Langerhans, an insulin-producing biological apparatus, to make them more acceptable when implanted in vivo (see O'Shea and Sun, *Diabetes* 35, 953 (1986) and Goosen et al. U.S. Pat. No. 4,673,566 (1987)). In another example, an ocular contact lens treated with a polyelectrolyte complex improves the properties of the lens (see Ellis and Salamone, U.S. Pat. No. 4,168,112 (1979)). Winterton et al. (U.S. Pat. No. 6,451,871 (2002)) disclose a method of making polyelectrolyte complexes on the surface of a contact lens by the multilayering method.

Protein adsorption is driven by the net influence of various interdependent interactions between and within surfaces and biopolymer. Possible protein-polyelectrolyte interactions can arise from 1) van der Waals forces 2) dipolar or hydrogen bonds 3) electrostatic forces and 4) hydrophobic effects. Given the apparent range and strength of electrostatic forces, it is generally accepted that the surface charge plays a major role in adsorption. However, proteins are remarkably tenacious adsorbers, due to the other interaction mechanisms at their disposal.

The use of thin films of polyelectrolyte complex for coating the interior surfaces of capillaries for CZE has been disclosed by Katayama and Ishihama (U.S. Pat. No. 6,586,065) and by Schlenoff and Graul (U.S. Pat. No. 6,402,918). Furthermore, Graul and Schlenoff (see *Analytical Chemistry*, 71, 4007 (1999)) describe how, in the analytical separation of proteins, the surface charge of the thin film of polyelectrolyte complex may be selected to have the same charge as the proteins being separated, thus preventing adsorption of the protein to the capillary. Preventing adsorption is considered advantageous in analytical CZE because the separation efficiency is greatly improved.

SUMMARY OF THE INVENTION

Among the aspects of the present invention may be noted the provision of pH sensitive PEMU films for coating the interior surfaces of microfluidic channels, such that the direction and magnitude of electroosmotic flow of aqueous compositions through the microfluidic channel may be controlled by pH. The resulting pH sensitive coated microfluidic channel surfaces may be used in applications for the selective adsorption of proteins and other electrostatically charged compositions into or onto such coatings to improve separation efficiency.

Briefly, therefore, the present invention is directed to a microfluidic device for carrying a liquid. The device comprises a microfluidic channel having an interior wall and a polyelectrolyte film on the interior wall whereby liquid carried by the channel contacts the polyelectrolyte film, the polyelectrolyte film having a thickness of about 1 to about 1000 nanometers and comprising an interpenetrating network of a predominantly positively charged polymer and a predominantly negatively charged polymer, the predominantly positively charged polymer, the predominantly negatively charged polymer or both containing (i) a pH insensitive positively or negatively charged repeat unit having a pKa greater than 9 or less than 3, and (ii) a pH sensitive repeat unit, the pH sensitive repeat unit having a pKa of 3 to 9, whereby the pH of liquid in the microfluidic channel may be used to control the velocity or direction of electroosmotic flow of the liquid within said microfluidic channel.

The present invention is further directed to a process of controlling the flow of liquid in a microfluidic channel. The process comprises changing the pH of liquid in the microfluidic channel to change the velocity or direction of flow of the liquid in the channel, wherein the microfluidic channel has an interior wall and a polyelectrolyte film on the interior wall whereby liquid carried by the channel contacts the polyelectrolyte film, and the polyelectrolyte film has a thickness between about 1 and about 1000 nanometers and comprises an interpenetrating network of a predominantly positively charged polymer and a predominantly negatively charged polymer, the predominantly positively charged polymer, the predominantly negatively charged polymer or both containing (i) a pH insensitive positively or negatively charged repeat unit having a pKa greater than 9 or less than 3, and (ii) a pH sensitive repeat unit, the pH sensitive repeat unit having a pKa of about 3 to 9.

The present invention is further directed to a process of derivatizing the surface of a microfluidic channel. The method comprises alternately passing solutions comprising positively charged and negatively charged polyelectrolytes through the microfluidic channel to form a polyelectrolyte film on the inner surface of the channel, the film having a thickness between about 1 and about 1000 nanometers and comprising an interpenetrating network of a predominantly positively charged polymer and a predominantly negatively charged polymer, the predominantly positively charged polymer, the predominantly negatively charged polymer or both contain (i) a pH insensitive positively or negatively charged repeat unit having a pKa greater than 9 or less than 3, and (ii) a pH sensitive repeat unit, the pH sensitive repeat unit having a pKa between 3 and 9 and complex in contact with the interior surface of a microfluidic channel whereby the pH of liquid in the microfluidic channel may be used to control the velocity or direction of electroosmotic flow of the liquid within said microfluidic channel.

Other objects and aspects of the invention will be, in part, pointed out and, in part, apparent hereinafter.

DETAILED DESCRIPTION OF THE PREFERRED EMBODIMENT(S)

Figure 1:
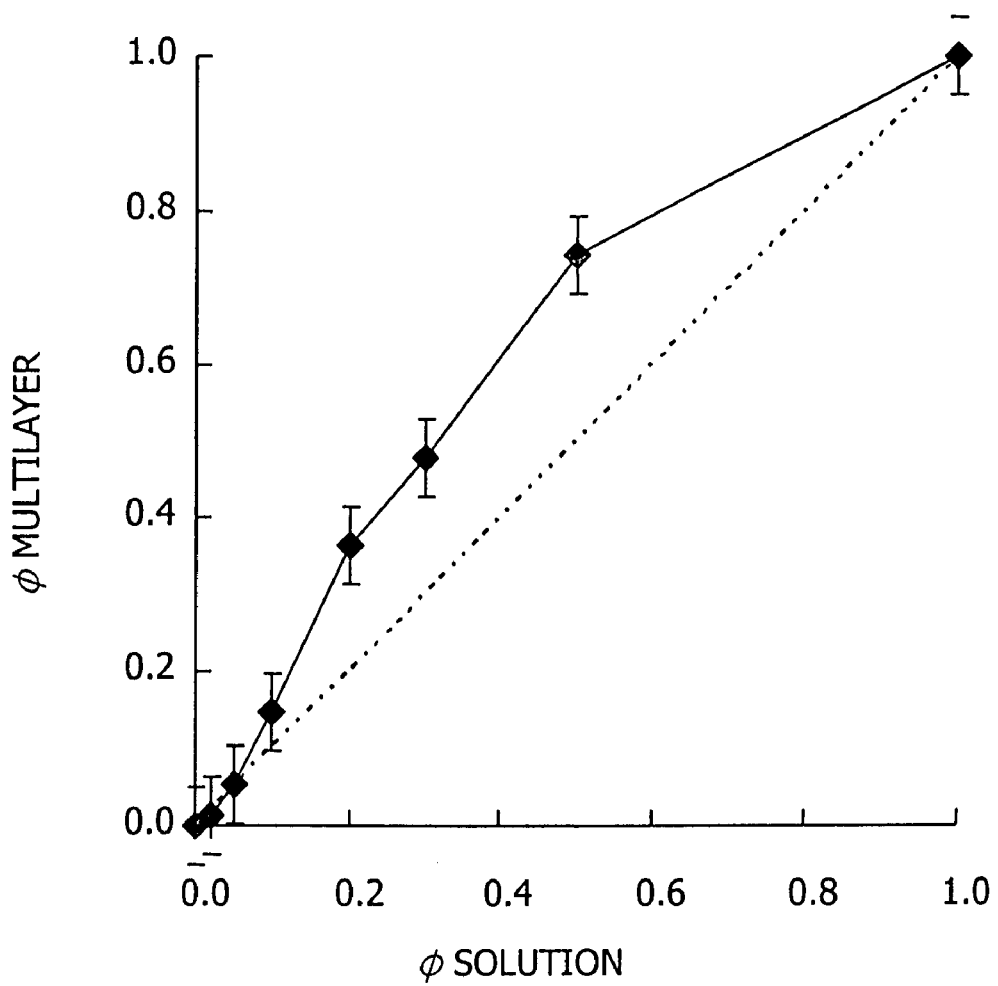
FIG. 1 shows the mole fraction of the copolymer PDADMA-co-PAA in the multilayer ($\phi_{multilayer}$) versus in the polycation solution ($\phi_{solution}$). According to the protocol of example 2, (copolymer$_\phi$-blend-PDADMA$_{1-\phi}$/PSS)$_{10}$ @ 1 M NaCl @ pH 2 was deposited on a silicon wafer. The dotted line shows "ideal" multilayer blend formation, for the case where the mole faction in the PEMU is the same as the mole fraction in solution.

In accordance with the present invention, the direction and magnitude of electroosmotic flow (EOF) of an aqueous buffer composition within microfluidic passages, or microfluidic channels, may be controlled by coating the interior surfaces of such microfluidic channels with a polyelectrolyte complex film. The polyelectrolyte complex film comprises pH sensitive repeat units, and according to the aqueous buffer composition pH, the pH sensitive repeat units may be protonated or deprotonated, charged or uncharged. As a result, the selection of film composition and aqueous buffer composition pH allows for the control of the polarity and density of the charge on the interior surface of the capillary, such that the coated interior surface may have an overall negative charge state so that EOF is in the "normal" direction (i.e., from positive electrode to negative electrode), or the coated interior surface may have an overall positive charge state so that EOF is in the "reverse" direction (i.e., from negative electrode to positive electrode). Advantageously, the magnitude of the EOF in either direction, which is influenced by the extent of polyelectrolyte complex film charge, may also be controlled by the aqueous buffer composition pH.

Those skilled in the art will recognize that round or rectangular cross-section geometries are common for microfluidic channels (see *Microfluidics and BioMEMS Applications*. F. E. H. Tay, Editor; Kluwer; Boston, 2002). It is known that microfluidic channels may be linear, curved, or, in order to provide as much length as possible, may follow a tortuous path. In addition, microfluidic channels may intersect in X-junctions, T-junctions, L-junctions, Y-junctions or other types of crossings. The cross-section diameter of microfluidic channels falls in the range between 1 and 1000 micrometers, preferably 10-200 micrometers. In one embodiment, the microfluidic channels are fused silica capillaries, the exterior coated with polymer, preferably polyimide, to impart mechanical strength. The silica capillaries are preferably of internal diameter 10 to 500 micrometers, and more preferably 30 to 150 micrometers. The inner surface of said capillaries are coated with a pH sensitive polyelectrolyte complex of thickness 1 nanometer to 1000 nanometers, preferably 10 to 100 nanometers.

A microfluidic device may comprise one microfluidic channel, or a plurality of microfluidic channels. For example, it is recognized by those skilled in the art that several parallel microfluidic channels permit a greater throughput of samples. Furthermore, microfluidic channels following different paths may intersect on the device for the purposes of mixing, reaction or detection. Therefore, in one preferred embodiment, one or more of a plurality of microfluidic channels on a microfluidic device is coated with pH sensitive polyelectrolyte complex.

It is well known to those skilled in the art that microfluidic channels may be fashioned from a variety of materials. For example, microfluidic channels may be formed in glass, silica, silicon, plastic, and metals. In one embodiment, the microfluidic channels to be coated are formed by photolithographic etching in silica. In another embodiment, the microfluidic channels are formed by machining grooves in plastic. In another embodiment, the microfluidic channels are formed by the curing of a polymer-forming material, such as a polysiloxane, inside a mold. In yet another embodiment, the microfluidic channels are formed by stamping a plastic surface with a master bearing the microfluidic channel pattern.

In one embodiment of this invention, the polyelectrolyte complex is formed on a polymer or plastic surface. Polyelectrolyte complexes, especially those formed by the layer-by-layer alternating deposition technique, are known by those skilled in the art to adhere to plastic materials. For example, Chen and McCarthy (*Macromolecules*, 30, 78 (1997) describe the layer-by-layer deposition of polyelectrolyte complex on poly(ethylene terephthalate). Even fluorinated polymers, such as Dupont's Teflon™, are known to be coated by polyelectrolyte complex using the layer-by-layer technique (see Hsieh et al. *Macromolecules*, 30, 8453 (1997). Barker et al. (*Analytical Chemistry*, 72, 5925 (2000)) (see also Locascio et al. U.S. Pat. Pub. No. 2002/0053514) have disclosed the layer-by-layer deposition of polyelectrolytes on plastic microfluidic channels. Thus, preferred substrates from which microfluidic channels may be formed and coated with polyelectrolyte complex include polycarbonate, poly(methyl methacrylate), polystyrene, poly(ethylene terephthalate), polysulfone, or polyamide.

In one embodiment of this invention, different sections of a microfluidic channel device are coated with polyelectrolyte of different composition, at least one section comprising pH sensitive multilayers. For example, a microfluidic channel comprises a length coated with non-pH sensitive polyelectrolyte complex, followed by a section coated with pH sensitive complex. In another embodiment, a microfluidic channel is formed by disposing a lid over a microfluidic channel pattern within a substrate, as described in Barker et al. (*Analytical Chemistry*, 72, 5925 (2000)), and either the lid or the channel, or both lid and channel, are coated with pH sensitive polyelectrolyte complex. In another embodiment, one or more arms of a microfluidic junction are coated with pH sensitive polyelectrolyte complex.

Generally, the polyelectrolyte complex film of the present invention comprise polyelectrolytes having a polyvinyl backbone and functional groups in monomeric repeat units. The PEMUs comprise polyelectrolytes bearing permanently charged functional groups and ionizable functional groups on monomeric repeat units. Preferably, the charge of the ionizable functional groups depends upon conditions in the solutions to which the PEMUs are exposed. In one embodiment, the groups are pH sensitive, that is, the state of protonation can be changed by a change of the pH within a range of about pH 2 to about pH 11 of an aqueous solution to which the PEMU is exposed. For example, they may have a pKa within a range surrounding physiological pH, which is approximately 7.4. For example, it is generally preferred that the pH sensitive ionizable groups have a pKa in the range of 3 to 9.

A. Polyelectrolytes for Multilayer Films

The oppositely charged polymers (i.e., polyelectrolytes) used to form the films are water and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly(diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive and negative repeat units distributed throughout the polymer in a random, alternating or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic. An example of a zwitterionic repeat unit is 3-[2-(acrylamido)-ethyldimethyl ammonio]propane sulfonate, AEDAPS. Preferably, polyelectrolytes comprising zwitterionic groups also comprise pH sensitive units. These pH sensitive units are preferably acrylic acids such as acrylic acids, methacrylic acid, carboxylic acids, and copolymers thereof, and protonatable nitrogens, such as pyridines, imidazoles, piperidines, and primary, secondary or tertiary amine groups, such as allylamine. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units.

The charges on a polyelectrolyte may be derived directly from the monomer units or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly (ether ether ketone) (SPEEK), poly(ethylenesulfonic acid), poly(methacryloxyethylsulfonic acid), their salts, and copolymers thereof; polycarboxylates such as poly (acrylic acid) (PAA) and poly(methacrylic acid).

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; and protonated polyamines such as poly(allylaminehydrochloride) (PAH) and polyethyleneimine (PEI).

Some synthetic polyelectrolytes used in accordance with the present invention generally become charged at certain pH values. For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte of a polyelectrolyte at the surface of, or within, a polyelectrolyte multilayer.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

Further examples of oppositely-charged polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule comprises a protonated sub-unit (e.g., protonated amines). Some negatively charged biomacromolecules comprise a deprotonated sub-unit (e.g., deprotonated carboxylates). Examples of biomacromolecules which may be charged for use in accordance with the present invention include proteins, polypeptides, enzymes, DNA, RNA, heparin, alginic acid, chondroitin sulfate, chitosan, chitosan sulfate, cellulose sulfate, polysaccharides, dextran sulfate, carrageenin, sulfonated lignin, and carboxymethylcellulose.

Natural, or biological, polyelectrolytes typically exhibit greater complexity in their structure than synthetic polyelectrolytes. For example, proteins may comprise any combination of about 2 dozen amino acid building blocks. Polymeric nucleic acids such as DNA and RNA may also comprise many different monomer repeat units. The sign and magnitude of the charge on proteins depends on the solution pH, as the charge on proteins is carried by weak acids, such as carboxylates (—COOH), or weak bases, such as primary, secondary, and tertiary amines. Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte typically comprises about 0.01% to about 40% by weight of a polyelectrolyte solution, and preferably about 0.1% to about 10% by weight.

Many of the foregoing polymers/polyelectrolytes, such as PDADMA and PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention.

Many of the foregoing polyelectrolytes have a very low toxicity. In fact, poly(diallyldimethylammonium chloride), poly(2-acrylamido-2-methyl-1-propane sulfonic acid) and their copolymers are used in the personal care industry, e.g., in shampoos. Also, because the polyelectrolytes used in the method of the present invention are synthetic or synthetically modified natural polymers, their properties (e.g., charge density, viscosity, water solubility and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Since some solvents are known to be incompatible with some plastic materials, preferred solvents for depositing polyelectrolyte complex thin films on plastics are water and alcohols.

Examples of polyelectrolytes that are soluble in water include poly(styrenesulfonic acid), poly(2 acrylamido-2-methyl-1-propane sulfonic acid), sulfonated lignin, poly(ethylenesulfonic acid), poly(methacryloxyethylsulfonic acid), poly(acrylic acids), poly(methacrylic acids) their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), protonated polyamines, such as, poly(allylamine hydrochloride) and poly(ethyleneimmine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonic acid), poly(diallyldimethylammonium chloride), poly(N-methylvinylpyridinium) and poly(ethyleneimmine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

In one embodiment of this invention, the charged polyelectrolyte is a synthetic copolymer comprising two or more charged repeat units, at least one of the repeat units being pH sensitive and the other repeat unit being pH insensitive, that is, maintaining the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

It is understood that the term "pH sensitive," as applied to a functional group, refers to a functional groups that exhibits differing degrees of ionization over the working pH range of the experiment, while pH insensitive refers to functional groups that maintain the same charge (either positive or negative) over the working pH range of the experiment.

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly (acrylic acids), poly(methacrylic acids), poly(carboxylic acids), and copolymers thereof. Additional preferred polyelectrolytes comprise protonatable nitrogens, such as poly (pyridines), poly(imidazoles), poly(piperidines), and poly (amines) bearing primary, secondary or tertiary amine groups, such as poly(allylamine). Preferred polyelectrolyte repeat units and their structures for use in the PEMUs of the present invention are shown in Table I.

TABLE I

Polyelectrolyte Repeat Units for building PEMUs

| Name | Structure |
|---|---|
| diallyldimethyl-ammonium (PDADMA) | 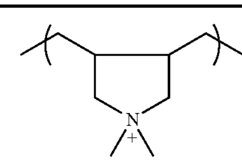 |
| acrylic acid (PAA) | 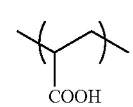 |
| allylamine (PAH) | 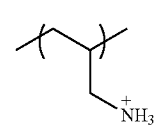 |

TABLE I-continued

Polyelectrolyte Repeat Units for building PEMUs

| Name | Structure |
|---|---|
| styrenesulfonic acid (PSS) | 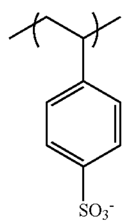 |
| diallyldimethyl-ammonium-co-acrylic acid (PDADMA-co-PAA) | X and Y denote proportions of repeat units |
| 1-methyl-2-vinylpyridinium (PM2VP) | X and Y denote proportions of repeat units |
| 1-methyl, 4-vinyl-imidazole (QPVI) | X and Y denote proportions of repeat units |
| 1-methyl-2-vinylpyridinium-co-polyethylene-oxide (PM2VP-co-PEO) | X and Y denote proportions of repeat units |

To avoid disruption, and possible decomposition, of the polyelectrolyte complex films preferred polyelectrolytes are copolymers comprising both pH sensitive and pH insensitive charged functionality on the same molecule. In one embodiment the negatively charged pH insensitive charged repeat unit comprising a polyelectrolyte is selected from the group consisting of styrenesulfonic acid, 2-acrylamido-2-methyl-1-propane sulfonic acid, sulfonated lignin, ethylenesulfonic acid, methacryloxyethylsulfonic acid, sulfonated ether ether ketone. In another embodiment the positively charged pH insensitive repeat unit comprising a polyelectrolyte is selected from the group consisting of diallyldimethylammonium, vinylbenzyltrimethylammonium, ionenes, acryloxyethyltrimethyl ammonium chloride, methacryloxy(2-hydroxy)propyltrimethyl ammonium, N-methylvinylpyridinium, other N-alkylvinyl pyridiniums, a N-aryl vinyl pyridinium, alkyl- or aryl imidazolium.

A range of positively charged and negatively charged pH insensitive repeat units may be included in the predominantly positively charged polymer, the predominantly negatively charged polymer, or both. In one embodiment, the pH insensitive repeat unit is a positively charged repeat unit selected from the group consisting of repeat units containing a quaternary nitrogen atom a sulfonium ($S^+$) atom, or a phosphonium atom. Thus, for example, the quaternary nitrogen may be part of a quaternary ammonium moiety ($—N^+R_aR_bR_c$ wherein $R_a$, $R_b$ and $R_c$ are independently alkyl, aryl or mixed alkyl and aryl), a pyridinium moiety, a bipyridinium moiety or an imidazolium moiety, the sulfonium atom may be part of a sulfonium moiety ($—S^+R_dR_e$ wherein $R_d$ and $R_e$ are independently alkyl, aryl or mixed alkyl and aryl) and the phosphonium atom may be part of a phosphonium moiety ($—P^+R_fR_gR_h$ wherein $R_f$, $R_g$ and $R_h$ are independently alkyl, aryl or mixed alkyl and aryl). In another embodiment, the pH insensitive repeat unit is a negatively charged repeat unit selected from the group consisting of repeat units containing a sulfonate ($—SO_3^-$), a phosphate ($—OPO_3H^-$), or a sulfate ($—SO_4^-$). For illustrative purposes, certain of these moieties are illustrated below:

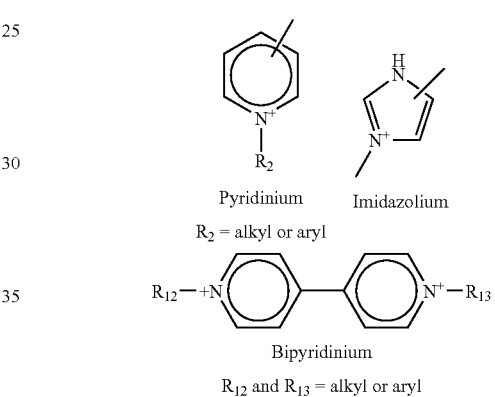

Pyridinium    Imidazolium $R_2$ = alkyl or aryl

Bipyridinium $R_{12}$ and $R_{13}$ = alkyl or aryl

In one embodiment, the copolymer comprising pH sensitive and pH insensitive units is formed by chemical modification of precursor polymers. The level of modification is preferably incomplete, leaving a mixture of pH sensitive and pH insensitive units on the same molecule. For example, poly(vinylimidazole) is preferably partially alkylated to yield pH insensitive imidazolium repeat units (as a result of alkylation) and pH sensitive repeat units (the vinylimidazole units that were not alkylated). A level of pH insensitive charge is required, sufficient to hold the multilayer together as the internal ionization is varied. Therefore, preferred levels of chemical modification to produce pH insensitive units are from 10-90% and more preferably from 20-80%. Preferred polymers for partial alkylation also include poly(vinyl pyridines) and poly(amines).

The preferred ratio of pH sensitive functional group to pH insensitive charged functional group enables control of surface and/or bulk charge without leading to disruption of the thin polyelectrolyte complex film. Thus ratios of pH sensitive functional group to pH insensitive charged functional group are preferably in the range 1:10 to 10:1, and more preferably in the range 2:10 to 10:2. Similarly, the total percentage of pH sensitive functional group is preferably between 5% and 95%.

In one embodiment of the present invention, the pH sensitive ionizable group is an imidazole repeat unit having the structure:

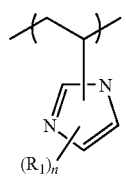

wherein each $R_1$ is independently hydrogen, or optionally substituted alkyl, aryl, alkaryl, heterocyclo, alkoxy, aryloxy, alkaryloxy, alkyl ester, aryl ester, alkaryl ester, alkyl amide, aryl amide or alkarylamide, and n is 0 to 2. Exemplary heterocycles include piperidinyl, pyrazinyl, purinyl, oxazolyl, isoxazolyl, thienyl, furyl, pyridinyl and the like. Representative substituents include alkyl, aryl, heterocyclo, hydroxyl, alkoxy, amino and the like. Preferably neither nitrogen-ring atom is quaternary and the imidazole ring is linked to the polyvinyl backbone via a ring carbon. In addition, each $R_1$ is hydrogen or lower alkyl, more preferably each $R_1$ is hydrogen. If $R_1$ is other than hydrogen, it is preferably unsubstituted lower alkyl.

An exemplary polycation satisfying these conditions is quaternized polyvinylimidazole (QPVI) which comprises about 60 mol % alkylvinylimidazolium repeat units and unquaternized polyvinylimidazole repeat units. The quaternized groups provide permanent charge and may be alkylated with higher carbon alkyl groups to impart hydrophobicity upon the permanently charged groups. The unquaternized imidazole groups provide pH sensitivity to the polycation. The pKa of the imidazole group is about 5.23, which allows charge switching under mild, slightly acidic, buffer conditions. Advantageously, the unquaternized imidazole group is relatively hydrophilic, as shown by a log partition coefficient which is about −0.8. Exemplary polyvinylimidazoles and polyvinylimidazoliums are shown in Table II. Table II also lists the pKas of each pH sensitive imidazole group.

TABLE II

| Name | Vinylimidazoles repeat units Structure[1] | pKa |
|---|---|---|
| N-vinyl-imidazole | | 6.07 |
| 1-methyl,4-vinyl-imidazole | | 5.45 |
| 4(5)-vinyl-imidazole (PVI) | | 6.19 |
| 1-methyl-5-vinyl-imidazole | | 5.28 |
| 1-butyl-5-vinyl-imidazole | | 7.02 |
| 1-butyl, 5-vinyl-imidazole-co-4(5)-vinyl-imidazole | | 5.01 |
| 1-butyl, 4-vinyl-imidazole-co-4(5)-vinyl-imidazole | | 5.12 |

[1]X and Y denote proportions of repeat units.

Optionally, the polyelectrolyte comprising imidazole repeat units also comprises an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, and vinyl caprolactam. The structures of these uncharged repeat units are shown in Table III.

It is also known by those skilled in the art that zwitterionic functional groups are also effective at resisting the adsorption of biomacromolecules, such as proteins (e.g. see Holmlin et al. Langmuir, 17, 2841 (2001)). In one embodiment, the polyelectrolyte complex film has a base surface which contacts the interior wall of a microfluidic channel, a solution-film interface surface which contacts liquid in a microfluidic channel, and an imaginary midpoint between these surfaces. Since zwitterionic groups are effective at resisting biomacromolecule adsportion, in one embodiment, at least 75% of the zwitterionic repeat units are present in the region of the film between the solution-interface surface and the midpoint, preferably at least 90% of the zwitterionic repeat units reside in the region of the film within 10 nanometers of solution-film interface surface. In one embodiment of this invention, films of polyelectrolyte complex also comprise zwitterionic functional groups and are used to coat the inner surfaces of microfluidic channels. It has been found that polymers comprising zwitterionic functional groups alone do not form polyelectrolyte complexes by the layer-by-layer technique if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. For control of bulk and surface charge of polyelectrolyte complexes for the purposes of controlling electroosmotic flow in microfluidic systems, polyelectrolytes comprising zwitterionic groups also comprise pH sensitive units. These pH sensitive units are preferably acrylic acids such as acrylic acids, methacrylic acid, carboxylic acids, and copolymers thereof, and protonatable nitrogens, such as pyridines, imidazoles, piperidines, and primary, secondary or tertiary amine groups, such as allylamine. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio] propane sulfonate) (PAEDAPS) and poly(N-propane sulfonate-2-vinyl pyridine) (P2PSVP). The structures of these zwitterions are shown in Table IV.

TABLE III

Neutral Repeat Units for use in PEMUs

| Name | Structure |
|---|---|
| acrylamide | 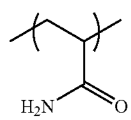 |
| vinylpyrrolidone | 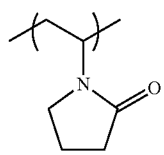 |
| vinylcaprolactam | 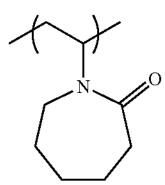 |

TABLE IV

Zwitterionic Repeat Units for use in PEMUs

| Name | Structure |
|---|---|
| 3-[2-(acrylamido)-ethyldimethyl ammonio] propane sulfonate (AEDAPS) | 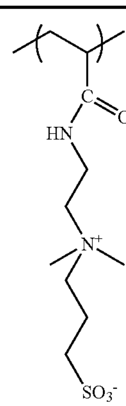 |

TABLE IV-continued

Zwitterionic Repeat Units for use in PEMUs

| Name | Structure |
|---|---|
| N-propane sulfonate-2-vinyl pyridine (2PSVP) | |

It has been disclosed by Graul and Schlenoff (*Analytical Chemistry*, 71, 4007 (1999)) that polyelectrolyte thin films prepared by the multilayering method are able to control the adsorption of protein. The adsorption of basic proteins (that is, those with a positive net charge at the operating pH) is preferably minimized by terminating the polyelectrolyte complex film with a positive charge, which repels the positive proteins. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) chemistry: biotechnical and biomedical applications*, Plenum Press: New York, 1992.) Yang and Sundberg (U.S. Pat. No. 6,660,367) disclose materials comprising ethylene glycol units that are effective at resisting the adsorption of hydrophilic proteins in microfluidic devices. In the present invention, copolymers of poly(ethylene oxide), PEO, or poly(ethylene glycol) PEG, are preferred materials for surface modification. The ethylene oxide (or ethylene glycol) repeat units are preferably present as blocks within a block copolymer. Preferably, the block copolymer also comprises blocks of charged repeat units, allowing the material to be incorporated into a polyelectrolyte complex. Sufficient ethylene oxide repeat units are required to promote resistance to protein adsorption, but too many ethylene oxide units do not allow polyelectrolyte complexes to associate. Therefore, the preferred ratio of charged to neutral blocks in a polyelectrolyte complex comprising a thin film for microfluidic flow control is from 10:1 to 1:4, and a more preferred ratio is 5:1 to 1:2.

In one embodiment of this invention, the polyelectrolyte complex comprises a stratum, in contact with a surface, that comprises pH insensitive polyelectrolytes, capped by a stratum comprising pH sensitive polyelectrolyte in contact with the solution. In one embodiment, the polyelectrolyte complex film has a base surface which contacts the interior wall of a microfluidic channel, a solution-film interface surface which contacts liquid in a microfluidic channel, and an imaginary midpoint between these surfaces. The polyelectrolyte complex film may comprise a pH sensitive stratum predominately located in the region of the film between the imaginary midpoint and the solution-film interface. It is known by those skilled in the art that such combinations of such strata may be prepared by the multilayering technique (see Dubas et al. *Journal of the American Chemical Society*, 123, 5368, (2001)). Preferred pH insensitive polyelectrolytes include polyelectrolytes comprising a sulfonate group ($-SO_3^-$), such as poly(styrenesulfonic acid) (PSS), poly(2-acrylamido-2-methyl-1-propane sulfonic acid) (PAMPS), sulfonated poly (ether ether ketone) (SPEEK), sulfonated lignin, poly (ethylenesulfonic acid), poly(methacryloxyethylsulfonic acid), their salts, and copolymers thereof; and polyelectrolytes comprising a quaternary ammonium group, such as poly(diallyldimethylammonium chloride) (PDADMA), poly (vinylbenzyltrimethylammonium) (PVBTA), ionenes, poly (acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof. In another embodiment the pH insensitive polyelectrolyte is selected from a group of polyelectrolytes that contain protonatable functionality, but that have pKa's outside the range of experimental use. For example, poly(ethylenimine) has protonatable amine functionality with pKa in the range 8-10, and is thus fully charged (protonated) if the experimental conditions do not surpass a pKa of about 7. In one embodiment, at least 55% of the pH sensitive units are present in the region of the film between the solution-interface surface and the midpoint, preferably at least 90% of the pH sensitive units are present in the region of the film between the solution-interface surface and the midpoint, and even more preferably, at least 50% of the pH sensitive units reside in the region of the film within 10 nanometers of solution-film interface surface. In a preferred embodiment of this invention the pH sensitive stratum is a layer formed by a single immersion into a solution comprising pH sensitive polyelectrolyte. In another preferred embodiment, the single immersion is made into a solution comprising a continuously variable mixture of pH sensitive and pH insensitive polyelectrolytes. Said pH sensitive strata preferably comprise between 5% and 90% pH sensitive units.

To assist in maintaining the physical integrity of the polyelectrolyte thin film comprising pH sensitive units, in one preferred embodiment a small amount of chemical crosslinking is introduced into the film. Crosslinking is preferably accomplished by including difunctional monomers in the polyelectrolytes comprising the thin film. For example, a divinyl repeat unit added to the polymerization reaction will be incorporated into two polyelectrolyte chains, giving a crosslink at the connection point. Alternatively, a polyelectrolyte film may be treated with a difunctional crosslinking agent. A preferred crosslinking agent is a dihalogenated compound, such as an aromatic or aliphatic dibromide, which is able to alkylate residual unalkylated units on two adjoining polyelectrolyte chains. Another preferred method of crosslinking a formed polyelectrolyte thin film is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (Macromolecules, 36, 8590 (2003)) is by the addition of a carbodiimide, which activates chemical crosslinking. The level of crosslinking is preferably 0.01 percent to 50%, and more preferably 0.1% to 10%.

It is occasionally advantageous to bind biomacromolecules within a microfluidic channel and to release them later on. In one embodiment of this invention, a pH sensitive polyelectrolyte film coating the inside of a microfluidic channel is maintained at a pH where the surface charge is opposite to the net charge of the biomacromolecule. It has been shown (e.g. see Ladam et al. *Biomacromolecules*, 1, 674 (2000)) that a polyelectrolyte complex thin film surface having an opposite charge to that on a biomacromolecule will cause said biomacromolecule to adsorb to the surface of the polyelectrolyte complex film. Therefore, a preferred mode of use of the pH sensitive polyelectrolyte thin film, coating the inside of a microfluidic channel, is to select operating conditions where said thin film is of opposite charge to a biomacromolecule, which conditions lead to the adsorption of the biomacromolecule to the film surface. Consequently, when the biomacromolecule is to be released, the operating conditions are changed so that said biomacromolecule is released from the polyelectrolyte thin film. Preferable operating conditions are control of pH when pH sensitive polyelectrolyte complex thin films are employed.

B. Additives for Use in Building PEMUs

The PEMUs of the present invention may be built by incorporating additives in the polyelectrolyte solutions which affect the thin film mechanical properties, solvation, and ability to absorb/release charged molecules. Optionally, the polyelectrolyte solutions may comprise one or more "salts." A "salt" is defined as a soluble, ionic, inorganic compound that dissociates to stable ions (e.g., sodium chloride). A salt is included in the polyelectrolyte solutions to control the thickness of the adsorbed layers. More specifically, including a salt increases the thickness of the adsorbed polyelectrolyte layer. In general, increasing the salt concentration increases the thickness of the layer for a given spray coverage and contact time. This phenomenon is limited, however, by the fact that upon reaching a sufficient salt concentration, multilayers tend to dissociate. Typically, the amount of salt added to the polyelectrolyte solution is about 10% by weight or less.

Both dip coating and spraying permit a wide variety of additives to be incorporated into a film as it is formed. Additives that may be incorporated into polyelectrolyte multilayers include inorganic materials such as metallic oxide particles (e.g., silicon dioxide, aluminum oxide, titanium dioxide, iron oxide, zirconium oxide and vanadium oxide) and clay minerals (e.g., hectorite, kaolin, laponite, montmorillonite and attapulgite). For example, nanoparticles of zirconium oxide added to a polyelectrolyte solution or complex solution tend to improve the abrasion resistance of the deposited film. See Rosidian et al., *Ionic Self-assembly of Ultra Hard $ZrO_2$/polymernanocomposite Films*, Adv. Mater. 10, 1087-1091.

C. Methods of Deposition

While this invention employs polyelectrolyte complex thin films, a preferred method of depositing said complex is by the alternating layer-by-layer deposition method. The preferred concentration for solutions comprising polyelectrolytes to be deposited is in the range 0.01 weight percent to 10 weight percent, and preferably 0.1 weight percent to 1 weight percent. The preferred method of alternating exposure of the microfluidic channel surface to the polyelectrolyte solutions is to alternately pump said solutions through the microfluidic channel, said pumping achieved by pressure- or EOF-driven flow.

The alternating polyelectrolyte layering method, however, does not generally result in a layered morphology of the polymers with the film. Rather, the polymeric components interdiffuse and mix on a molecular level upon incorporation into the thin film. See Lösche et al., *Macromolecules* 31, 8893 (1998). Thus, the polymeric components form a true molecular blend, referred to as a "polyelectrolyte complex," with intimate contact between polymers driven by the multiple electrostatic complexation between positive and negative polymer segments. The complexed polyelectrolyte within the film has similar morphology as a polyelectrolyte complex formed by mixing solutions of positive and negative polyelectrolyte. It is also known that although there is extensive intermingling of neighboring layers over a range of 4-6 nominal layers, it is possible to obtain actual layers of different composition, or strata, by interspersing several layers made from one pair of polyelectrolytes by several layers made from a different pair. See Lösche et al., *Macromolecules* 31, 8893 (1998). For example, if polymers A and C are positively charged and polymers B and D are negatively charged, about 3 or 4 pairs of A/B layers followed by about 3 or 4 pairs of A/D or C/D layers will produce two strata of distinct composition.

Alternatively, the thin film coating may be applied to a surface using a pre-formed polyelectrolyte complex. See Michaels, *Polyelectrolyte Complexes, Ind. Eng. Chem.* 57, 32-40 (1965) and Michaels (U.S. Pat. No. 3,467,604). This is accomplished by mixing the oppositely-charged polyelectrolytes to form a polyelectrolyte complex precipitate which is then dissolved or re-suspended in a suitable solvent/liquid to form a polyelectrolyte complex solution/dispersion. The polyelectrolyte complex solution/dispersion is then applied to the substrate surface and the solvent/liquid is evaporated, leaving behind a film comprising the polyelectrolyte complex. To aid in dissolution or dispersion of the complex, both a salt, such as sodium bromide, and an organic solvent, such as acetone are added to the solution comprising the precipitated complex. It is known that the material obtained by layering two polyelectrolytes is substantially the same as material obtained by mixing and precipitating said polymers to form a polyelectrolyte complex.

For fast throughput and coating of surfaces, one method of applying the polyelectrolyte complex is by alternate spraying of a surface. Spraying is especially preferred when applying the coating to large areas using alternating exposure of oppositely-charged polyelectrolyte solutions. Spraying alternating oppositely-charged polyelectrolyte solutions has several advantages over the Michaels coating and evaporation method, including: improved control over film thickness especially the ability to make extremely thin thicknesses (e.g., less than about 1 µm), enhanced uniformity of film thickness especially over uneven surfaces and contours, and films may be produced without the use of organic solvents which may require precautions to avoid negative health and/or environmental consequences. The solutions may be sprayed onto a substrate by any applicable means (e.g., an atomizer, an aspirator, ultrasonic vapor generator, or entrainment in compressed gas). In fact, a hand operated "plant mister" has been used to spray the polyelectrolyte solutions. Typically, the droplet size in the spray is about 10 nm to about 1 mm in diameter. Preferably, the droplet size is about 10 µm to 100 µm in diameter. The coverage of the spray is typically about 0.001 to 1 mL/cm$^2$, and preferably about 0.01 to 0.1 mL/cm$^2$. Preferably, a microfluidic channel pattern within a substrate is sprayed separately from the lid and the lid and microfluidic channel pattern are then assembled to form the complete, enclosed microfluidic channel passage.

The duration in which the polyelectrolyte solution is typically in contact with the surface it is sprayed upon (i.e., the contact time) varies from a couple of seconds to several minutes to achieve a maximum, or steady-state, thickness. The contact duration is selected based on the desired relationship between throughput (i.e., the rate at which alternating layers are created) and layer thickness. Specifically, decreasing the contact duration increases throughput and decreases layer thickness whereas increasing the duration decreases throughput and increases thickness. Preferably, the contact time is selected to maximize the throughput of layers that have a satisfactory thickness and are uniform across the surface.

Other preferred methods of depositing the polyelectrolyte solutions and/or polyelectrolyte complex include casting, dip coating and doctor blading. Particularly preferred methods are dip coating and spraying.

Rinsing, to remove nonadsorbed polyelectrolyte, between the application of each polyelectrolyte solution is preferred. The rinsing liquid comprises an appropriate solvent (e.g., water or organic solvent such as alcohol). Preferably the solvent is water. If the solvent is inorganic (e.g., water), the rinsing liquid may also comprise an organic modifier (e.g., ethanol, methanol or propanol). The concentration of organic modifier can be as high as less than 100 percent by weight of the rinsing liquid, but is preferably less than about 50 percent by weight. The rinsing liquid may also comprise a salt (e.g., sodium chloride) which is soluble in the solvent and the organic modifier, if included in the rinsing liquid. The concentration of salt is preferably below about 10 percent by weight of the rinsing liquid. It should be noted that as the concentration of organic modifier increases the maximum solubility concentration of salt decreases. The rinsing liquid, however, should not comprise a polyelectrolyte. The rinsing step may be accomplished by any appropriate means (e.g., flushing, dipping or spraying). Preferably, the rinsing step is accomplished by flushing. For spray rinsing, the amount of waste is preferably reduced by recycling the polymer solutions removed from the surface. Optionally, prior to depositing the second through n$^{th}$ layer of sprayed oppositely charged polyelectrolyte solution, the surface of the multilayer structure may be dried.

Particles with diameters ranging from nanometers to millimeters may also be coated with polyelectrolyte complex. If the alternate layering method is used, it is not practical to coat particles individually. Neither is the spray method practical, unless particles are larger than about 100 Am. Instead, batches of particles are alternately immersed in coating solutions, with intervening rinse, as detailed by Caruso and Sukhorukov, Chapter 12 in *Multilayer Thin Films*, G. Decher and J. B. Schlenoff, Eds., Wiley-VCH, Weinheim, 2003. See also Donath et al. U.S. Pat. Pub. No. 2003/0219384.

In another embodiment, the polyelectrolyte complex is deposited on or adsorbed to at least a portion of the surface of the stationary phase of a chromatographic medium such as particulate chromatographic column packing material, the interior of capillary tubes as used for capillary electrophoresis chromatography (see, U.S. Pat. No. 6,402,918 and U.S. Pat. No. 6,841,054 which are hereby incorporated by reference in their entireties for all purposes), or a porous continuous solid often referred to as a monolithic stationary phase (see Zou et al., *Monolithic stationary phased for liquid chromatography and capillary electrochromatography*, Journal of Chromatography A, 954, 5-32 (2002)).

If a column comprising particles coated with multilayer is to be employed, it is preferred to first pack the column with particles, and then alternately flow through solutions of polyelectrolyte and rinse. This approach is advantageous because it avoids damaging the gel-like polyelectrolyte complex films during batch manipulation and coating. Further, such an in-situ coating procedure helps to cement the individual particles together and makes the column more resilient.

In yet another embodiment of the present invention the polyelectrolyte complex is a coating or layer on a substrate or substratum and may be deposited according to any appropriate method (see, e.g., supra, as a multilayer or as a pre-formed polyelectrolyte complex). The substratum may be non-porous or porous and may be comprised of many types of materials that are well known in the art such as polymers, metals, and ceramics. The surface of polymeric support materials may be positively charged by comprising tetraalkyl ammonium groups, negatively charged by comprising sulfonate groups, or neutral. In another embodiment, the substratum is porous and comprises a material selected from the group consisting of polypropylene, nylon, polytetrafluoroethylene, glass, and alumina (all of which are known to those of skill in the art). Typically, the average size of the pores is between about 100 nm and about 10 μm and the degree of porosity is between about 0.1 and about 60%.

The following nomenclature for multilayers will be employed to describe PEMUs on substrates: $(A/B)_x$ where A is the starting polyelectrolyte contacting the substrate, B is the terminating polyelectrolyte in contact with subsequent protein solutions and x is the number of layer pairs. In $(A/B)_xA$, A would be the terminating polymer. Salt, MY (cation M and anion Y), has an important role in the buildup process and is represented by $(A/B)_x$@c MY, where c is the molarity of the salt (MY) in the polymer solution. The pH can be included in the nomenclature when using pH dependent PEMUs. For example, $(PAH/PAA)_2PAH$ @0.25M NaCl @pH 7.4, represents two layers pairs of PAH/PAA, terminated with a layer of PAH, built at 0.25 M NaCl and a pH of 7.4.

The following examples will further illustrate the present invention. The above described polyelectrolytes, additives, and deposition methods were used for building PEMUs of a variety of compositions on microfluidic channel substrates. The PEMUs, solutions, and additives were modified in various ways as shown in the examples, and the effects of those modifications on the ability of the PEMU to control the direction and magnitude of electroosmotic flow in a microfluidic channel was monitored using various quantitative and qualitative methods.

The PEMU compositions were selected to achieve precise control of flow through microfluidic channels. While the number of possible combinations is immense, the goal was to make some broad deductions concerning the role of pH sensitive repeat units, pH insensitive repeat units, hydrophilic repeat units, and zwitterionic repeat units on the direction and magnitude of electroosmotic flow and separations of charged molecules.

Example 1

Quantitative and Qualitative Techniques for Use in Characterizing PEMUs

The following techniques were used to characterize the PEMUs of the present invention. Transmission IR spectra were recorded with a Nicolet Avatar 360 FTIR spectrometer. The thickness of the dried multilayers was measured with a Gaertner Scientific L116S ellipsometer, using 632.8 nm light at 70° incidence angle. A refractive index of 1.55 was employed for multilayers. Atomic force microcopy, AFM (Dimension 3100, Digital Instruments) in Tapping Mode™ was used to track the multilayer surface morphology change.

ATR measurements were performed with a Nicolet Nexus 470 fitted with a 0.5 mL capacity flow-through ATR assembly (Specac Benchmark) using a 70×10×6 mm 45° germanium crystal. Each spectrum had 32 scans coadded at a resolution of 4 cm$^{-1}$. Multilayers were deposited on the ATR crystal while it was loaded in the flow cell by passing polyelectrolyte and rinse solutions, in an alternating manner, through the cell.

Example 2

Characterizing a PEMU System Comprising a Blend of Copolymer and Homopolymer as the Polycation A PEMU comprising a blend of two polyelectrolytes as the polycation was deposited on a silicon wafer and characterized. This blend was used as a coating on the interior surface of a capillary. See EXAMPLE 4. A random copolymer PDADMA-co-PAA (Calgon Merquat® 281, mol % of AA is 36%; $M_w$~200,000) was used as one polycation component. Homopolymer PDADMA (Aldrich, $M_w$=300,000-400,000) was also used as a polycation component. Polystyrene sulfonic acid, PSS, (Scientific Polymer Products, molecular weight, $M_w$~70,000) was used as the polyanion.

Silicon wafers (Si<100>, 0.5 mm thick, 1 in. diameter, undoped, double-side polished from Topsil Inc.) were cleaned in "piranha" solution (70% $H_2SO_4$ (conc.)/30% $H_2O_{2(aq)}$) and then in $H_2O_2$/ammonia/water 1:1:7 vol/vol, rinsed in distilled water and dried with a stream of $N_2$.

To prepare multilayers on these Si wafers they were affixed to a stainless steel shaft with Teflon™ tape. The shaft was rotated at 300 rpm by a small DC motor. A robotic platform (StratoSequence V, nanoStrata Inc.), accommodating eight 100 mL beakers, was programmed to expose the wafer alternately to the 1 mM polymer solutions, with acidic water rinses in between. The salt concentration (NaCl) in the deposition solutions was 1.0 M. The pH of both deposition solutions and rinsing water were adjusted to 2 by HCl.

The function of the permanent positive charges (quaternary ammoniums from PDADMA) is essentially to keep the multilayer stitched together at all pH values. Too many counterion-compensated units within a multilayer cause hyperswelling and decomposition (see Sukhishvili, S. A.; Granick, S. *Macromolecules,* 35, 301 (2002)). For example, we have used this same copolymer, which is commercially available (Merquat 280®, Calgon Inc.) as an ingredient for personal care products, to build pH-releasable multilayers (see Dubas et al. *Journal of the American Chemical Society.* 123, 5368 (2001)). Therefore the carboxylates were "diluted" by adding pure homopolymer PDADMA to the "polycation" solution. Since the concentration of PAA in the pure Merquat polymer is 36 mol %, the final concentration of carboxylates in the multilayer, expressed as a molar ratio or mole % of total PAA+PDADMA units, is given by $$PEMU mol\% \ PAA = \frac{[Merquat]}{[Merquat] + [PDADMA]} \times 36$$

An appropriate balance between sufficient copolymer to induce switching, yet not too much to cause film disruption, is required. In this Example, about 7 mol % PAA, or a mixture of 0.20 mM copolymer and 0.80 mM PDADMA, sufficed.

Since in this work a mixture of copolymer PDADMA-co-PAA and homopolymer PDADMA was used in the "cationic polyelectrolyte" solution for the PEMU buildup, the term for this polycation mixture is defined as copolymer-blend-PDADMA. The subscript "φ" describes the mole fraction of copolymer in the cationic buildup solutions. For example, (copolymer$_{0.2}$-blend-PDADMA$_{0.8}$/PSS)$_{10}$ @1.0M NaCl @pH 2, represents ten bilayers made from a solution 20 mol % PDADMA-co-PAA copolymer and 80 mol % PDADMA homopolymer, and a solution of PSS, built at 1.0 M NaCl and a pH of 2.

We verified, using FTIR of comparison samples on silicon wafers, that the multilayer carboxylate composition approximately reflects the solution composition from which the films are deposited. Ideally, the PAA component would be incorporated into the multilayer in the same proportion as copolymer in the mixed polycation solution. To ascertain whether this was, indeed, the case, the amount of copolymer in the multilayer was evaluated by transmission FTIR. Mole fractions of copolymer in the PEMU are plotted as a function of mole fraction in the polycation solution (FIG. 1). In the ideal case there would be no preference for either copolymer or homopolymer DADMA, giving a slope of 1.0 (dotted line). A positive deviation indicates some preference for copolymer. Notwithstanding the slight preference for copolymer, it is shown that PEMUs of continuously variable composition may be assembled by the blending strategy described.

Example 3

Stability of PEMUs to pH Shock

Figure 2:
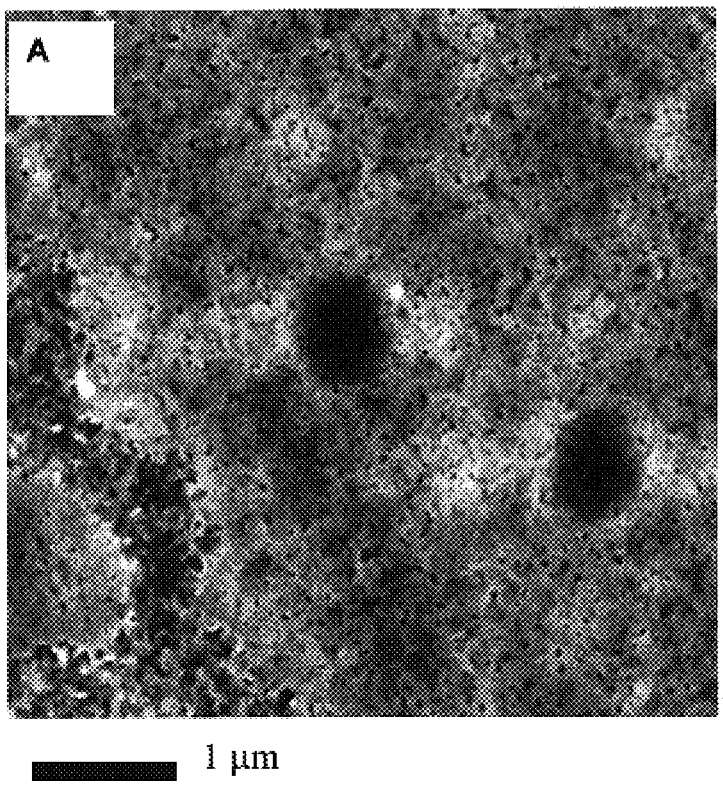
FIG. 2 is an AFM micrograph showing the surface topology of a polyelectrolyte multilayer, built according to the protocol of example 3, with a composition of copolymer$_{0.2}$-blend-PDADMA$_{0.8}$/PSS)$_{10}$ copolymer$_{0.2}$-blend-PDADMA$_{0.8}$ @1 M NaCl @pH 2 after exposure to a pH 11 solution.
Figure 3:
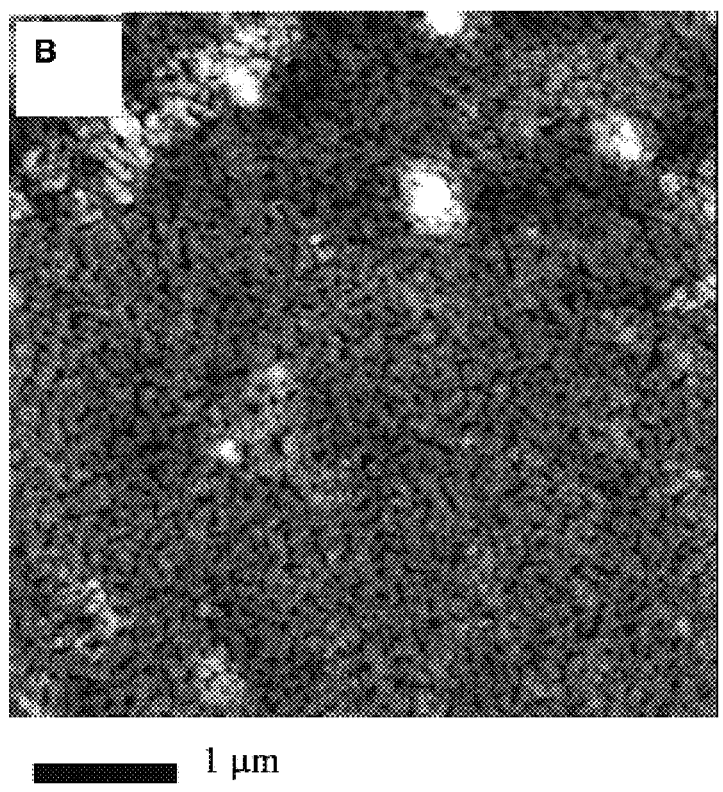
FIG. 3 is an AFM micrograph showing the surface topology of a polyelectrolyte multilayer, built according to the protocol of example 3, with a composition of (copolymer$_{0.2}$-blend-PDADMA$_{0.8}$/PSS)$_5$ copolymer$_{0.2}$-blend-PDADMA$_{0.8}$ @ 1 M NaCl @ pH 2 after exposure to a pH 11 solution.

A key variable in pH sensitive coatings was the total thickness of the PEMU. While it is desirable to minimize the number of layers deposited, a minimum number of layers are also required to mask the bare silica in a capillary. Microscopic investigations (Atomic Force Microscope) of 21-layer PEMUs on Si wafer revealed some evidence of pH-induced cratering in the surface, as seen in the micrograph in FIG. 2. PEMUs made with 11 layers showed no such topological nonidealities, as shown in the micrograph in FIG. 3. This difference was attributed to the loss of material from the surface of 21-layer PEMUs. Loss of thickness from multilayers on silicon wafers is evidence for not only polymer charge extrusion but also charge expulsion.

Figure 4:
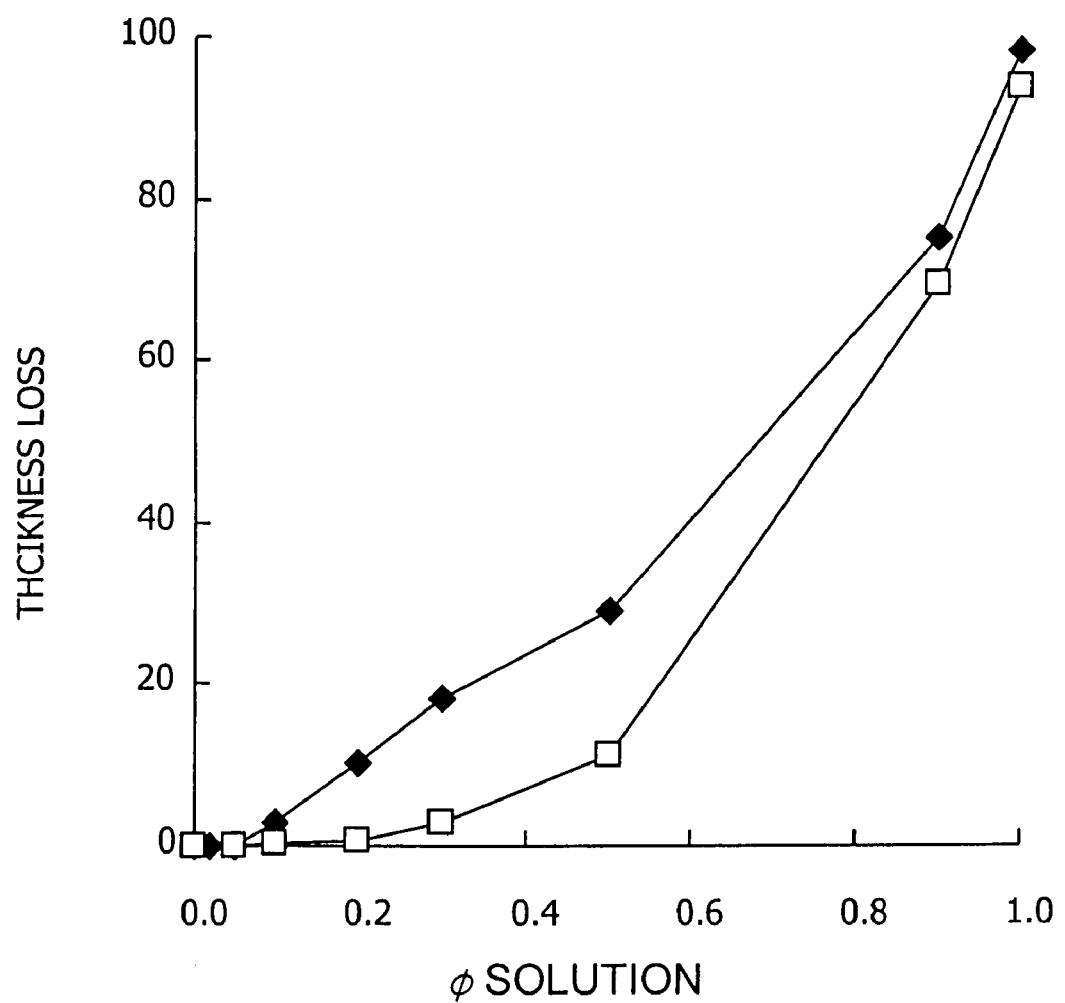
FIG. 4 shows thickness loss versus mole fraction of the copolymer in the polycation solution ($\phi_{solution}$). According to the protocol of example 3, (copolymer$_{100}$-blend-PDADMA$_{1-\phi}$/PSS)$_{10}$ @ 1 M NaCl @ pH 2 (♦) and (copolymer$_{100}$-blend-PDADMA$_{1-\phi}$/PSS)$_{10}$ copolymer$_\phi$-blend-PDADMA$_{1-\phi}$@ 1 M NaCl @ pH 2 (□) were deposited on a silicon wafer and then exposed to pH 11 solution for 60 minutes.

Multilayers were more stable as the content of pH-ionizable material decreased, and less stable when the last layer was negative as-deposited (PSS). To assess the stability of various combinations of PEMU, they were subjected to "pH shock" by immersion in pH 11 solution (adjusted by NaOH) for 60 minutes. Thicknesses were recorded before and after this treatment and the loss in thickness is plotted in FIG. 4 as a function of composition. At the extreme of pure copolymer, the entire multilayer is lost, as observed previously (see Dubas et al. *Journal of the American Chemical Society*, 123, 5368 (2001)). PEMUs made with pure PDADMA, on the other hand, were stable. For the blends, intermediate behavior was observed, which showed a dependence on the surface charge of the as-made PEMU: films terminated with the polycation mixture (□ in FIG. 4) were more resilient to pH jumps than those terminated with PSS. Films with negative surface charges (♦ in FIG. 4) exhibited erosion of polymer with any copolymer present, while positive-capped PEMUs with up to about a nominal copolymer mole fraction of 0.2 were stable.

Example 4

Coating of the Interior Surface of a Capillary with pH Sensitive Multilayers

Two PEMUs of different composition were deposited on the interior surface of a capillary. In both cases, polystyrene sulfonic acid, PSS, (Scientific Polymer Products, molecular weight, $M_w$~70,000) was used as the polyanion. For one PEMU, a random copolymer PDADMA-co-PAA (Calgon Merquat® 281, mol % of AA is 36%; $M_w$~200,000) was used as one polycation component, and homopolymer PDADMA (Aldrich, $M_w$=300,000-400,000) was used as a second polycation component. This polycation is referred to as a copolymer-blend-PDADMA. Polyethylenimine, PEI (branched, Sigma-Aldrich Inc.) was deposited as the first layer for this PEMU to improve adhesion.

A second PEMU used quaternized poly(4(5)-vinylimidazole) (QPVI) as the polycation. QPVI was synthesized as described by Overberger and Vorchheimer (*Journal of the American Chemical Society*, 85, 951 (1963)) and methylated using excess methyl iodide in a concentrated solution of the polymer in methanol. Elemental analysis showed the compound to be roughly 60% quaternized.

Ultrapure water (Barnstead E-pure) was used as the solvent for rinsing and preparing deposition solutions. The polyelectrolyte concentration of deposition solutions was 1 mM based on the polymer repeat unit. The citric buffer series, with a total ionic strength of 10 mM, was used to control pH in the range 2.78-7.30.

Electrophoresis was conducted on a Beckman Coulter P/ACE™ MDQ Capillary Electrophoresis System (Palo Alto, Calif.) with 254 nm UV detection operating at 15 kV and 25° C. Fused silica capillary (Polymicro Technologies Inc., Phoenix, Ariz.) with the dimension of 50 μm ID×31.2 cm (effective length 21 cm) was employed. Sample injection was performed by pressure (0.5 psi, 5 seconds).

Multilayer coatings were deposited using the rinse function on the Beckman CE system. For the copolymer-blend-PDADMA/PSS system, polymer deposition solutions contained 1 mM polymer, and 1 M NaCl. The capillary was first conditioned by a 30-min rinse of 1 M NaOH. The first layer of polymer (PEI, 10 mM) was deposited by rinsing the polymer solution through the capillary for 10 min followed by a 5 min pH 2.78 buffer rinse. PEI was added to promote adhesion of the multilayer to the silica tubing. All other layers were deposited with 5 min deposition time followed by a 5 min pH 2.78 buffer rinse. After the coating was completed, the tube was rinsed by pH 2.78 buffer for an hour.

For the QPVI/PSS system, polymer deposition solutions contained 1 mM polymer, and 0.5 M NaCl. The capillary was first conditioned by a 30-min rinse of 1 M NaOH. The first layer of QPVI was deposited by rinsing the polymer solution through the capillary for 10 min followed by a 5 min pH 7.3 buffer rinse. All other layers were deposited with 5 min deposition time followed by 5 min pH 7.3 buffer rinse. After coating, the capillary was rinsed with pH 7.3 buffer for an hour.

Acetone was used as a neutral electroosmotic flow marker. Electroosmotic mobility ($\mu_{eof}$) quantifies the electroosmotic flow and is given as the velocity of solvent flow per unit electric field strength [$cm^2$ $V^{-1}$ $s^{-1}$]. We use the convention that the "normal" direction, from positive electrode to negative electrode, is positive.

The fused silica capillaries, internal diameter 50 μm, in this Example are typical for this particular type of microfluidics application. The thin polyelectrolyte complexes coating the inside of these capillaries were made by the multilayering technique, using poly(styrene sulfonate), PSS, as a permanently charged negative polyelectrolyte, and a mixture of poly(diallyldimethylammonium chloride), PDADMA, and a random copolymer of diallyldimethylammonium and acrylic acid, PDADMA-co-PAA, (0.64/0.36 mole ratio of respective monomer units, rendering the copolymer net positive at all pH). Coatings were prepared in buffers at low pH with the last layer the copolymer (positive) having the carboxylic acid groups in the protonated (neutral) state. On exposure to sufficiently high pH, carboxylic groups are ionized, overwhelming the surface positive excess polymer charge, and therefore switching the surface charge to negative.

Figure 5:
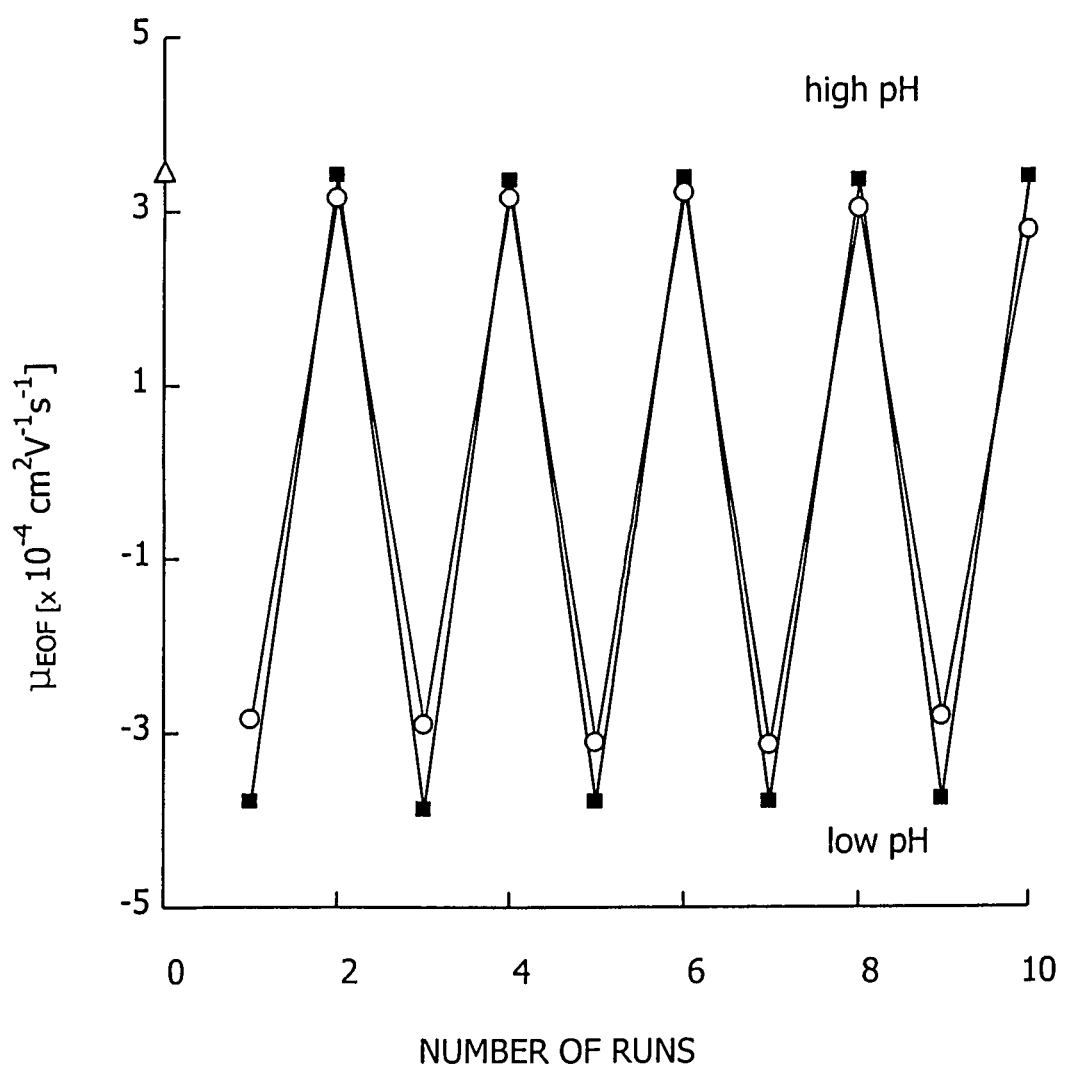
FIG. 5 is a graph showing run-to-run EOF switching reproducibility of two PEMU systems. According to the protocol of example 4, (1) an 11-layer PEMU of composition (copolymer$_{0.2}$-blend-PDADMA$_{0.8}$/PSS)$_5$copolymer$_{0.2}$-blend-PDADMA$_{0.8}$ @ 1 M NaCl @ pH 2 (■) and (2) a PEMU of composition (QPVI/PSS)$_5$ @ 0.5 M NaCl @ pH 7.3 (○) were built in a capillary. The open triangle is EOF for a bare capillary at pH 7.30. Even runs were in pH 7.30 buffer; odd runs at pH 2.78. Citric buffer at 10 mM total ionic strength. 15 kV applied voltage, 31.2 cm capillary. Positive EOF indicates the surface charge is negative.

FIG. 5 shows that the EOF of a capillary coated with an 11-layer PEMU of copolymer-blend-PDADMA/PSS (■, copolymer on top), where the positive layers were composed of 20% copolymer, exhibited very reproducible switching of flow direction with alternating between buffers of "high" (7.30) and "low" (2.78) pH. The fact that such flow reversal was observed for positive layers containing as little as 7.2 mol % AA units was initially surprising. However, when internal PAA is ionized, it is probable that the charge is extruded to the surface. Evidence for the motion of polyelectrolytes within multilayers has been acquired via atomic force microscopic measurements of PEMU surface smoothing (see Dubas and Schlenoff *Langmuir*, 17, 7725 (2001)). pH-induced phase separation of PAA-containing PEMUs, yielding porous films, has also been observed (see Mendelsohn et al. *Langmuir*, 16, 5017 (2000)).

Similar behavior was observed using the weak base polyvinylimidazole that was 60% quaternized to impart some permanent positive charges, quaternized polyvinylimidazole, or QPVI, with PSS as the multilayering partner (○). In this case, the QPVI was deposited from pH 7.3 citric buffer, which is above the pKa (about 6) of the imidazole repeat units, allowing extra positive charge to appear within the PEMU as the pH is lowered. As seen in FIG. 5, EOF switching of approximately the same magnitude as with the copolymer-blend-PDADMA/PSS is observed. Note that dilution of the PVI units is not required, due to the enhanced stability of the QPVI/PSS ion pair compared to the PDADMA/PSS ion pair.

Example 5 pH-Switching Polyelectrolyte Complex Comprising a Weak Base

Figure 6:
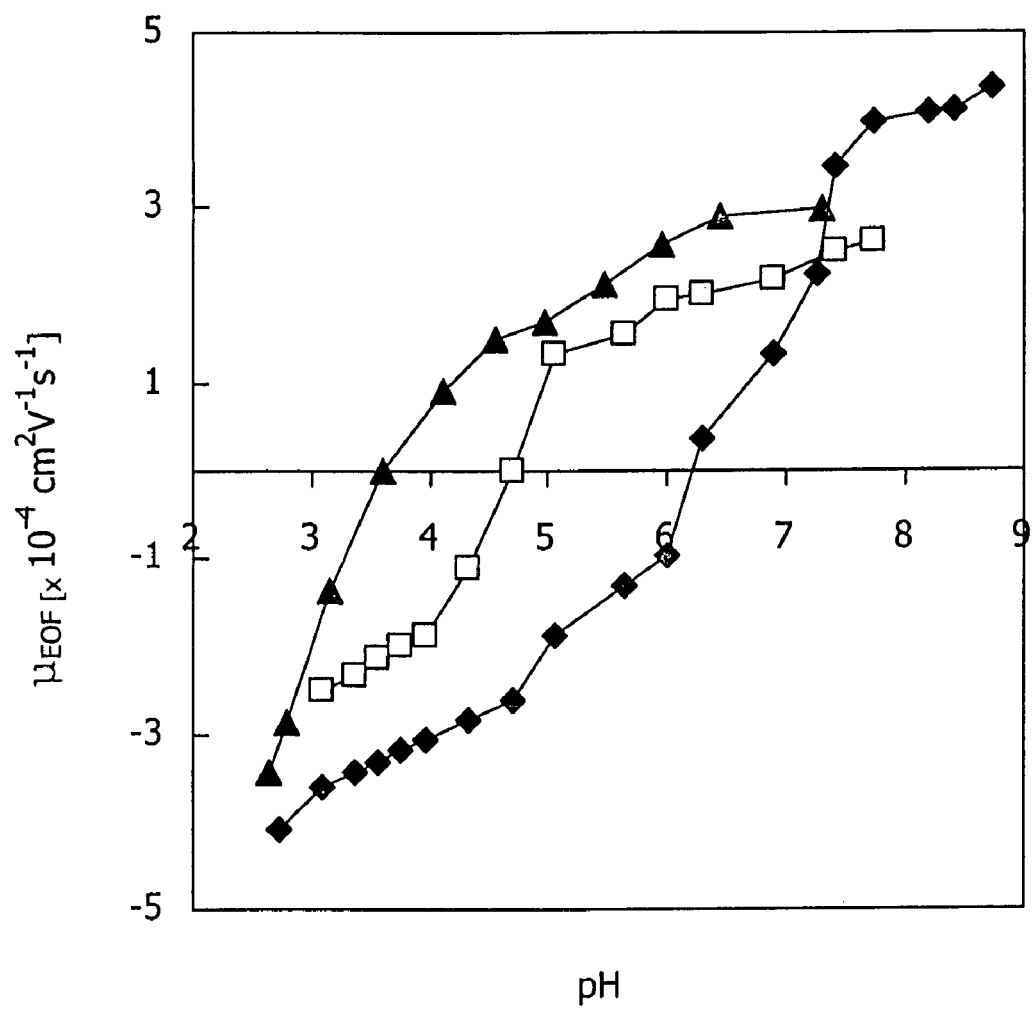
FIG. 6 shows EOF mobility versus pH. According to the protocol of example 5, multilayers ▲: (copolymer blend/PSS)$_5$ copolymer blend @ 0.5 M NaCl @ pH 2.72; □: (PM2VP/PSS)$_5$ @ 0.5 M NaCl @ pH 8.73; ♦: (QPVI//PSS)$_5$ @0.5 M NaCl @ pH 8.73 were deposited in a capillary. pH-of-zero-flow is 3.6, 4.7 and 6.2, respectively. The level of quaternization of PM2VP is about 85% and of QPVI is about 60%.

Fine control of EOF is possible by selection of intermediate pH for buffers. FIG. 6 depicts EOF as a function of pH for copolymer-blend-PDADMA/PSS, QPVI/PSS, and PM2VP/PSS multilayer coatings. All three reverse directions. For comparison, a bare surface simply offered a range of EOF on the positive ("normal") flow side. The pH-of-zero-flow, corresponding to the pH-of-zero-net-surface-charge, was initially presumed to occur at a point near the $pK_a$ of the acrylic acid, imidazole, or vinyl pyridine units within the multilayer. Although the switching buffers were chosen to bracket a pH of 5 (i.e. approximately the $pK_a$ of solution polycarboxylic acid or polyvinylimidazole), the pH-of-zero-charge may not coincide with the solution $pK_a$. It has been shown that the $pK_a$ of weak acid/base units within the PEMU is modified by their interaction with oppositely-charged polyelectrolyte units (see Rmaile and Schlenoff, *Langmuir*, 18, 8263 (2002)).

A single layer of PDADMA in contact with the interior surface of a fused silica capillary tube has previously been employed as a positive coating for silica capillaries in CZE (see Wang and Dubin, *Analytical Chemistry*, 71, 3463 (1999)). In the present invention, a single coating of PDADMA-co-PAA also afforded pH-controlled switching of EOF, but this single layer yielded irreproducible and unstable flows, due to contributions from the underlying silica silanol, which were insufficiently masked. Slow surface rearrangements may also impact negatively.

Figure 7:
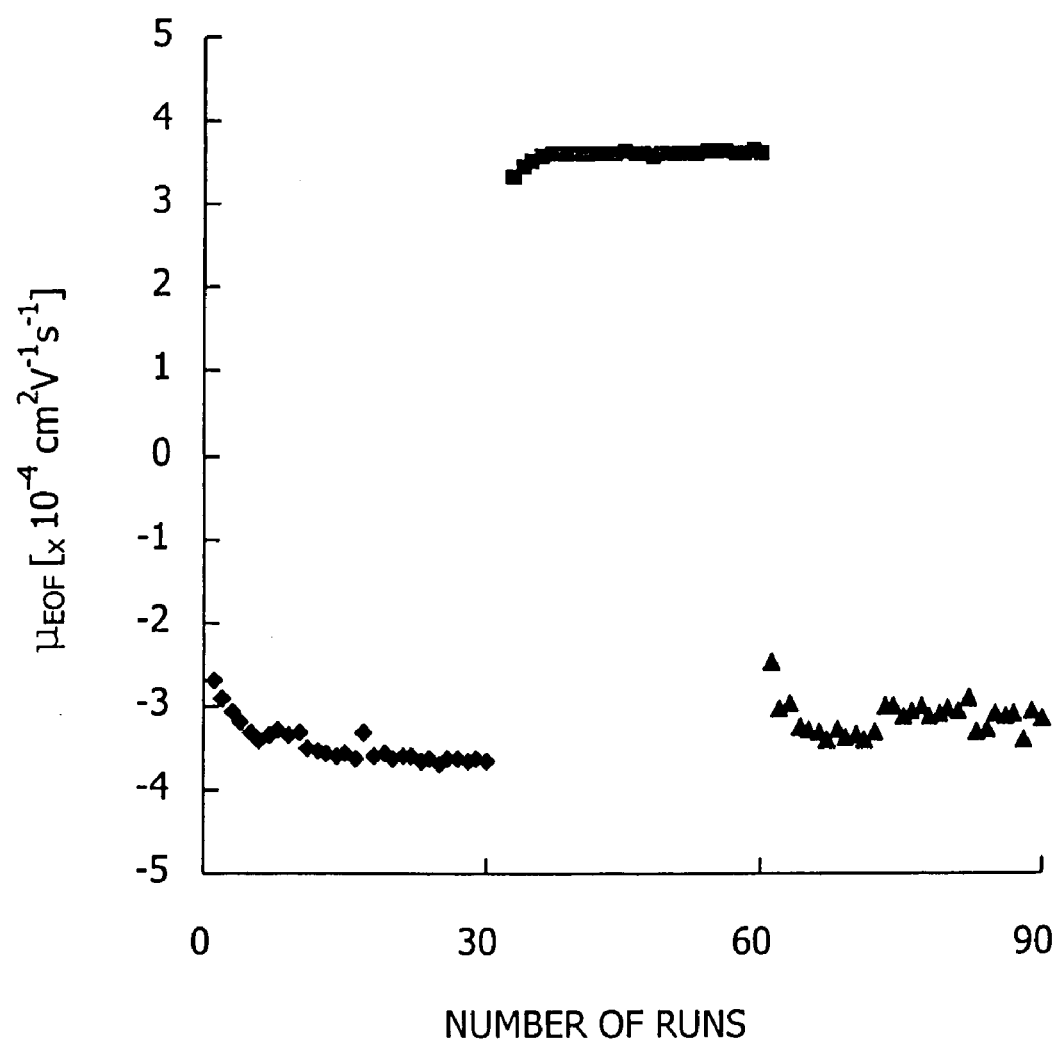
FIG. 7 shows EOF mobility v. number of runs with switching pH. According to the protocol of example 5, the PEMUs were built as follows: ▲: (copolymer blend/PSS)$_5$ copolymer blend @ 0.5 M NaCl @ pH 2.72 with the runs at pH 2.78; ■: (PM2VP/PSS)$_5$ @ 0.5 M NaCl @ pH 8.73 with the runs at pH 7.30; ♦: (QPVI//PSS)$_5$@0.5 M NaCl @ pH 8.73 with the runs at pH 2.78.

Run-to-run reproducibility was excellent and is illustrated by FIG. 7, which shows sequential runs following pH switching. After a short time the EOF is very stable. This contrasts strongly with the instability of EOF in bare capillaries in response to wide swings in pH. Other advantages of the present coating include the possibility to separate acidic and basic proteins on one column, either by choosing pH values that minimize irreversible adsorption of all components, or by switching the pH to release proteins that may have adsorbed to the surface. Additionally, choosing a pH where the EOF is truly zero (hard to accomplish in silica capillaries) allows separation based solely on electrophoretic mobility and may allow isoelectric focusing.

Example 6

A Multilayer Terminated with a Single Layer of pH-Ionizable Polymer

Figure 8:
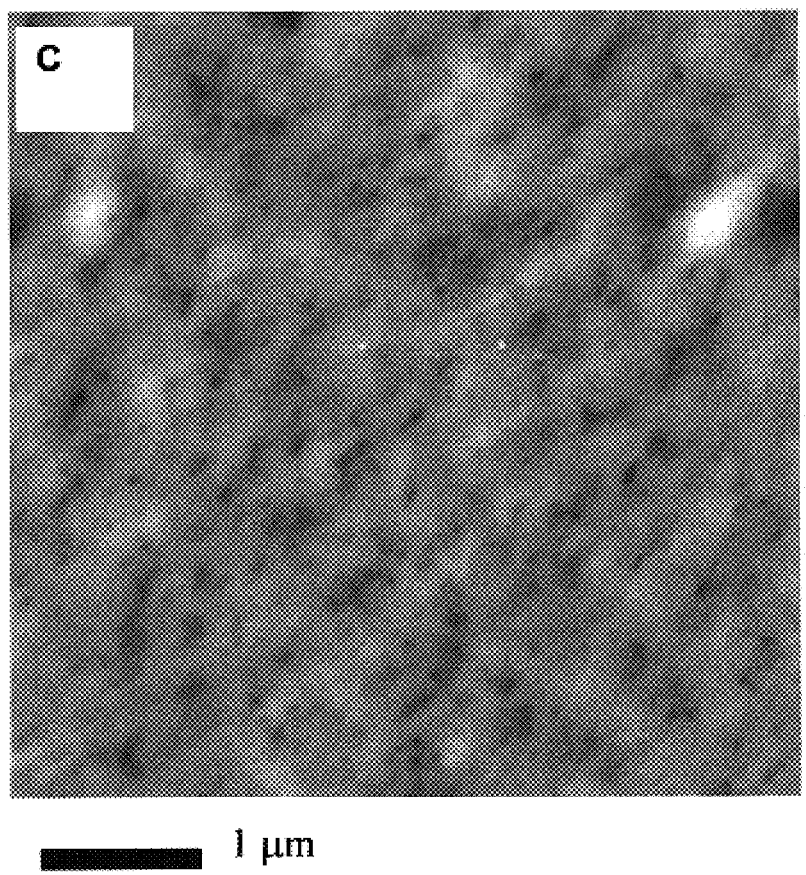
FIG. 8 is an AFM micrograph showing the surface topology of a polyelectrolyte multilayer built according to the protocol of example 6 with composition (PDADMA/PSS)$_5$ copolymer$_{0.2}$-blend-PDADMA$_{0.8}$ @ NaCl @ pH 2 after exposure to a pH 11 solution.

In order to reduce perturbations within the bulk, ionizable material was limited to the surface of the PEMU by employing the copolymer only in the last layer. For example, a multilayer was built from 5 layer pairs of PDADMA and PSS, pH-independent polymers, and terminated with polyelectrolyte comprising PAA. The micrograph in FIG. 8 shows the surface topology of $(PDADMA/PSS)_5 copolymer_{0.2}$-blend-$PDADMA_{0.8}$ @0.5M NaCl @pH 2, after switching between low and high pH. Very little evidence of disruption is seen with this surface-only ionizable multilayer, yet it performs effectively in controlling surface charge (vide infra).

Figure 9:
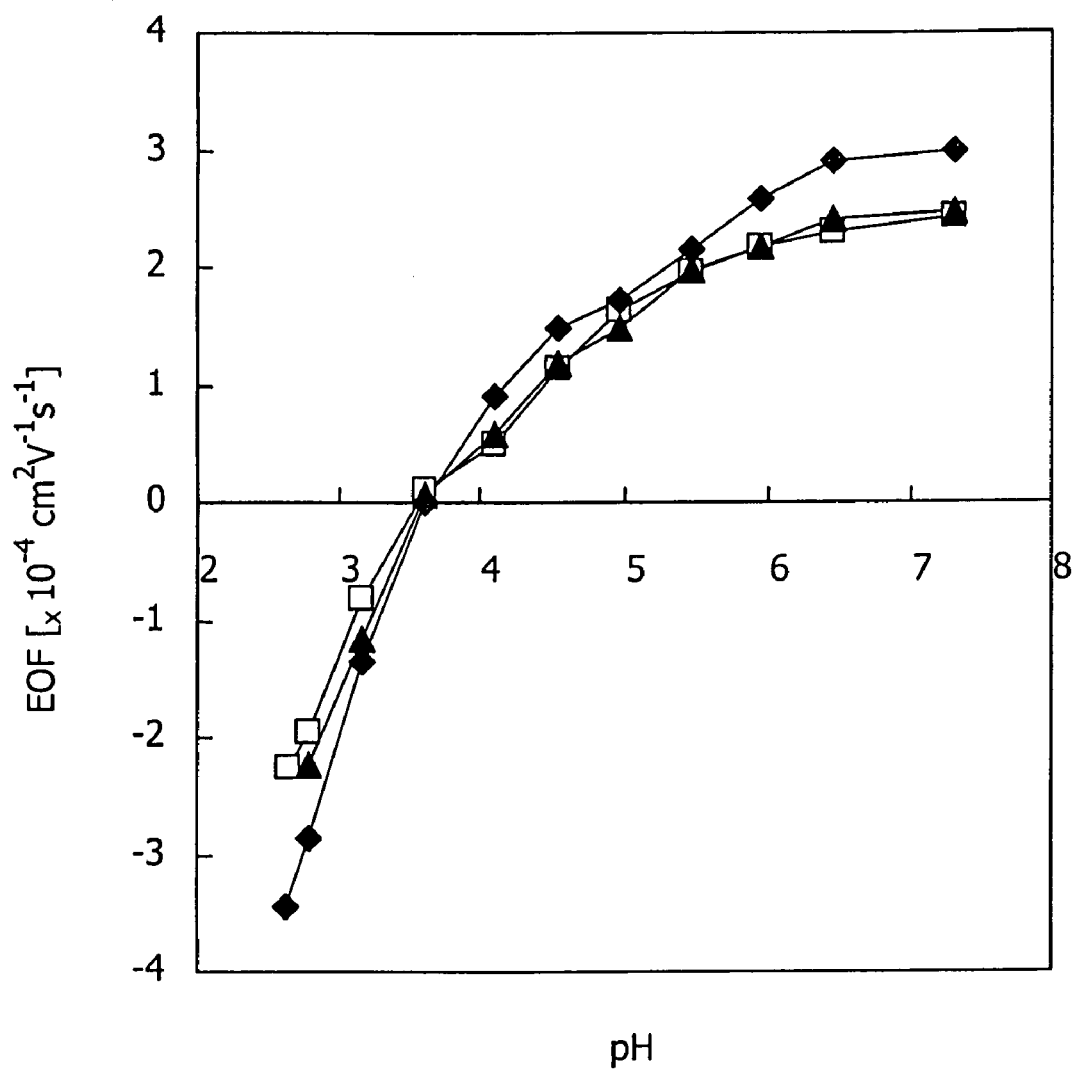
FIG. 9 shows EOF mobility as a function of pH for 3 films built according to the protocol of example 6 of composition: (□) (copolymer$_{0.2}$-blend-PDADMA$_{0.8}$/PSS)$_{10}$copolymer$_{0.2}$-blend-PDADMA$_{0.8}$ $_{@1}$ M NaCl @pH 2; (♦) (copolymer$_{0.2}$-blend-PDADMA$_{0.8}$/PSS)$_5$ copolymer$_{0.2}$-blend-PDADMA$_{0.8}$ @ 1 M NaCl @ pH 2; (▲) (PDADMA/PSS)$_5$ copolymer$_{0.2}$-blend-PDADMA$_{0.8}$ @ 1 M NaCl @ pH 2.

The single layer of ionizable material on top of a multilayer performs surprisingly well. FIG. 9 compares the EOF at various pH for $(copolymer_{0.2}$-blend-$PDADMA_{0.8}/PSS)_{10} copolymer_{0.2}$-blend-$PDADMA_{0.8}$ @1.0M NaCl @pH 2 with $(copolymer_{0.2}$-blend-$PDADMA_{0.8}/PSS)_5 copolymer_{0.2}$-blend-$PDADMA_{0.8}$ @1.0M NaCl @pH 2 and $(PDADMA/PSS)_5 copolymer_{0.2}$-blend-$PDADMA_{0.8}$ @1.0M NaCl @pH 2. Zero EOF corresponds to a net neutral effective surface charge. It is seen that an improvement is obtained with the more structurally stable "thinner" $(copolymer_{0.2}$-blend-$PDADMA_{0.8}/PSS)_{10} copolymer_{0.2}$-blend-$PDADMA_{0.8}$ @1.0M NaCl @pH 2 system.

A single "layer" of $copolymer_{0.2}$-blend-$PDADMA_{0.8}$ on top of $(PDADMA/PSS)_5$ @1 M NaCl@pH 2 gives performance (FIG. 9) that is indistinguishable from that of the 21-layer film (which contains 11 layers of $copolymer_{0.2}$-blend-$PDADMA_{0.8}$). This is a significant finding, as it shows how, by using only one pH sensitive layer on top of many non-pH sensitive layers, surface charge may be controlled without the drawback of major structural rearrangements shown above. (See Example 3.) Zero net surface charge, leading to zero EOF, is useful if transport through microfluidic channels must be driven only by electrophores is.

Figure 10:
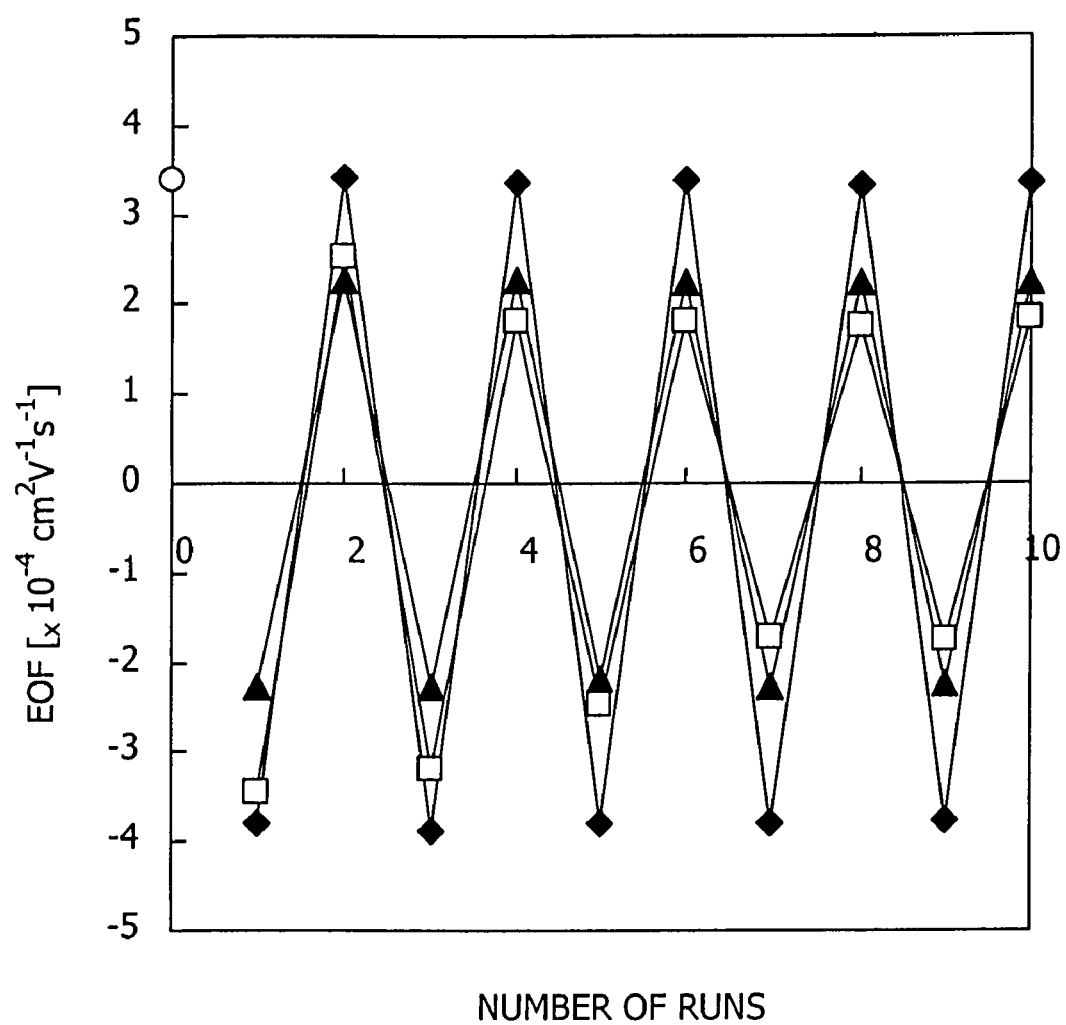
FIG. 10 is a graph showing EOF mobility of the PEMU coatings v. number of runs by switching between pH 2.78 and pH 7.30. According to the protocol of example 6: (□) (copolymer$_{0.2}$-blend-PDADMA$_{0.8}$/PSS)$_{10}$ copolymer$_{0.2}$-blend-PDADMA$_{0.8}$ @1 M NaCl @pH 2; (♦) (copolymer$_{0.2}$-blend-PDADMA$_{0.8}$/PSS)$_5$ copolymer$_{0.2}$-blend-PDADMA$_{0.8}$ @ 1 M NaCl @ pH 2; (▲) (PDADMA/PSS)$_5$ copolymer$_{0.2}$-blend-PDADMA$_{0.8}$ @ 1 M NaCl @ pH 2 were coated on the inside of the capillary column. Even runs were done at pH 7.30, a positive EOF indicated the surface charge was negative; odd runs were done at pH 2.78, a negative EOF indicated the surface charge was positive. The hollow circle represents the EOF of bare capillary.

FIG. 10 shows more detail of the performance of the multilayer coatings subjected to multiple pH switching. Two features may be noted here: first, quasistable switching of flow direction is possible. Second, the 21-layer film shows deterioration in flow rate, while the 11-layer and the $(copolymer_{0.2}$-blend-$PDADMA_{0.8})$-terminated PEMUs are more stable.

Figure 11:
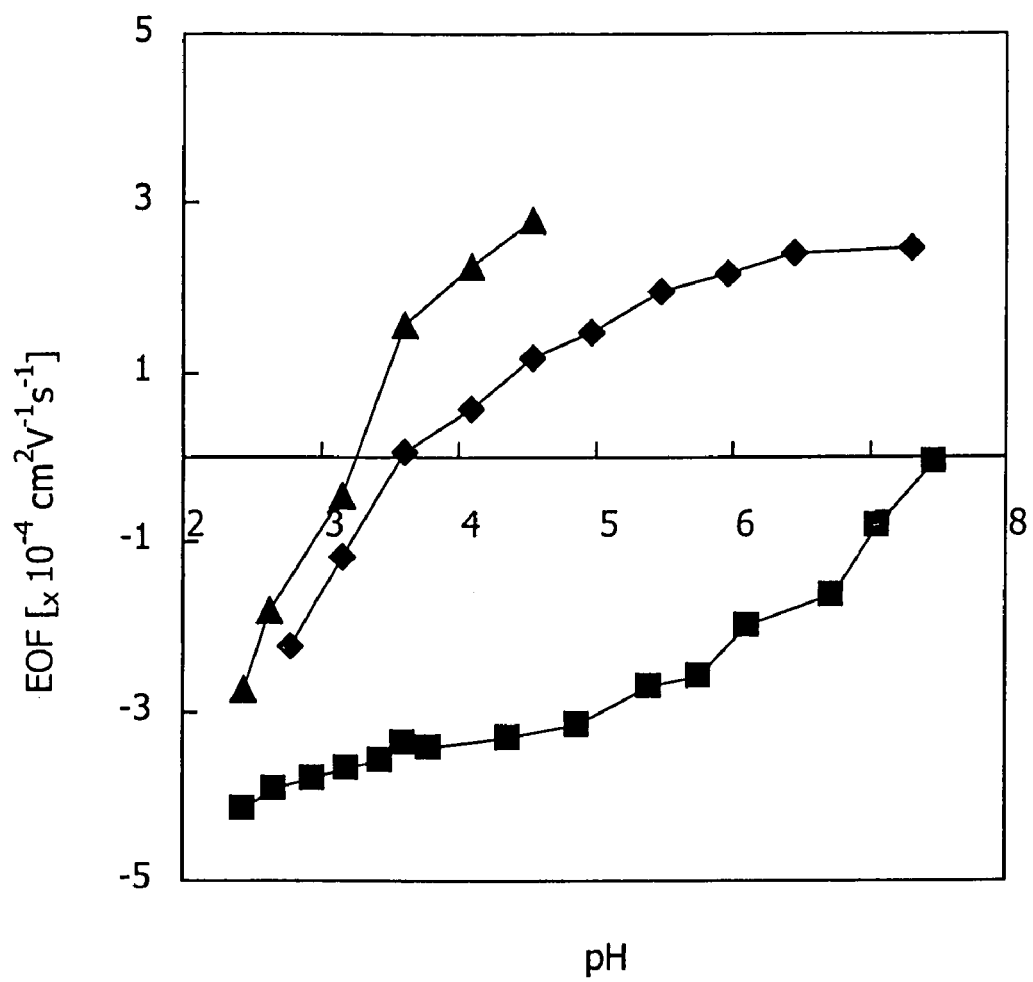
FIG. 11 shows EOF mobility v. pH response curves for (PDADMA/PSS)$_5$copolymer$_{101}$-blend-PDADMA$_{1-\Phi}$@ NaCl @ pH 2 multilayers built according to the protocol of example 6 where $\Phi$=0.05 (■), 0.2 (♦), and 1 (▲), respectively.

Since the strategy of terminating the multilayer with only one pH sensitive layer proved effective in EOF control, we investigated the dependence of surface charge reversal on the composition of the top layer. In FIG. 11, EOF v. pH response curves are shown for $(PDADMA/PSS)_5 copolymer_\phi$-blend-$PDADMA_{1-\phi}$ systems where $\phi$=0.05, 0.2, and 1 respectively.

It is seen that the higher the proportion of AA units, the lower the pH required for switching surface charge (flow direction)—more carboxylate functionality requires less ionization (lower pH) to overwhelm surface positive charges. This surface charge "titration" experiment showed that a minimum of about 5 mol % AA is required for switching. One advantage of varying the concentration of AA units is that one can select the pH for zero surface charge, which is useful for isoelectric focusing, or performing pure electrophoretic transport. It is surprising that such a low percentage of acrylic acid functionality on only the top layer is able to control or switch the surface charge (even taking into account the slight enrichment of AA within the PEMU shown in FIG. 1).

Example 7

Controlled Protein Adsorption on a pH-Switching Polyelectrolyte Complex Comprising Ionizable Groups FTIR (Nicolet Nexus 470 FTIR) was used in attenuated total internal reflection mode (ATR, Specac Inc., flow cell of volume 0.49 mL) to monitor protein adsorption onto polyelectrolyte multilayers assembled on an ATR cell housing a 70 mm×10 mm×6 mm 45° germanium (Ge) crystal. Multilayer buildup was done by alternately filling the ATR cell with polymers (1 mM in 0.25 M NaCl), with intervening rinses in water. Solution pH for buildup, including rinse, with PAH was stabilized with TRIS buffer (pH 7.4). The exposure time for each solution was 10 minutes. Multilayers for ATR were not dried before protein adsorption. A multilayer spectral background in buffer was taken prior to protein adsorption. Layer-by-layer buildup and protein adsorption were monitored using areas of characteristic bands of interest (sulfonate stretch for PSS, $v(SO_3^-)$, at ~1033 cm$^{-1}$ and amide II band at ~1540 cm$^{-1}$). All spectra were recorded using 32 scans and 4 cm$^{-1}$ resolution. After addition of protein solution to the ATR cell, the protein spectrum was monitored with time until there were no further significant changes in spectra, the cell was rinsed with buffer, and amide II peaks were integrated. $H_2O$ spectra were subtracted from raw infrared spectra. The amounts of proteins were calculated based on calibration curves for each protein.

UV-vis absorption spectra were recorded on quartz-supported multilayers using a Perkin Elmer UV/VIS/NIR spectrometer (Lambda 900). Fused quartz plates (2 mm thick, 1 inch diameter, GM Associates) were pretreated with "piranha" and then in $H_2O_2$/ammonia/water (1:1:7) then rinsed. Film thickness was estimated from multilayers deposited on the native $SiO_2$ layer (about 20 Å thick) on silicon wafers using the same conditions.

One of the objectives of the present invention is to create a protein-repelling multilayer comprising PAA, with the PAA limited to the surface. A composition gradient would be desirable where PEMU durability is an issue, since hydrophobic polyelectrolytes form less swollen and more resilient films. Thus, multilayers having a composition gradient, and therefore a hydrophilicity gradient, were prepared starting with PM2VP/PSS (relatively hydrophobic) and ending with PAA (relatively hydrophilic). Advantageously, one would preserve durability, but maintain surface repellency, with the hydrophilic polyelectrolyte limited to the outer, or outer few, layers. Also, using a specialized polymer as the outer layer only would help conserve a potentially costly material. Fibrinogen was used in this Example since it is relatively large and is a model for "sticky" serum proteins (e.g. see Mrksich et al. *Langmuir*, 11, 4383 (1995)).

Table V shows that a PEMU with a hydrophobic bulk (PM2VP/PSS), capped with a hydrophilic surface (PAH/PAA), shows no significant change in fibrinogen adsorption compared to a PEMU of uniform hydrophilic composition (PAH/PAA). A surface layer is thus able to "mask" protein adsorption properties of bulk PEMU material. Another polymer known to those skilled in the art for its effectiveness in preventing protein adsorption is poly(ethylene oxide), PEO, also known as poly(ethylene glycol), PEG (e.g. see Harris, *Poly(ethylene glycol) chemistry: biotechnical and biomedical applications*, Plenum Press: New York, 1992). The ability of hydrophilic repeat units to reduce protein adsorption was also seen in other experiments comparing protein adsorption on PEMUs made from PM2VP-block-PEO (Table I) and PSS, with those made from PM2VP and PSS and capped with one layer of PM2VP-block-PEO. The economical use of one layer only of diblock copolymer proved as effective as making the entire PEMU from the diblock.

TABLE V

| Hydrophilicity/hydrophobicity gradient for fibrinogen adsorption | | |
|---|---|---|
| Multilayer | Surface Charge | Γ, mg/m$^2$ |
| (PAH/PAA)$_3$ | — | 0.34 ± 0.1$^a$ |
| (PM2VP/PSS/PM2VP) (PAA/PAH/PAA) | — | 0.41 ± 0.1$^a$ |
| (PM2VP/PSS)$_3$ | — | 3.4 ± 0.5$^a$ |

$^a$Measured with ATR-FTIR

All proteins are rather "sticky"—capable of adsorbing via electrostatic (including "patch charge" type adsorption), hydrogen bonding and "hydrophobic" interactions. Surfaces of opposite charge to that of the protein were found to be more effective at promoting protein adsorption. Where such electrostatic interaction dominates, increased ionic strength was shown generally to decrease protein adsorption. Also evident was the partial effectiveness of a hydrophilic neutral block (PEO) at preventing access to the charged surface beneath it. Protein adsorption was found to be enhanced at multilayers with opposite charge. In fact, the thickness of the PEMU was shown to play an important role in the adsorption process, since the PEMU can act as a "sponge" or a matrix to load proteins. Direct ATR-FTIR measurement on thicker PEMUs confirmed protein penetration into the multilayer matrix for oppositely charged surfaces, whereas AFM revealed islands of surface aggregate for like-charged multilayers. On exposure to solution of higher ionic strength, sorbed protein could be released by an ion exchange type mechanism.

Example 8 pH-Switching Polyelectrolyte Multilayers Comprising Ionizable Functionality and Zwitterionic Groups Zwitterionic polyelectrolytes comprise repeat units that bear a negative and a positive charge. Opposite charges on a repeat unit are in relatively close proximity and therefore have an opportunity to interact strongly. Because the zwitterion group is charge balanced (charge neutral) it does not require counterions when in solution.

Given that opposite charges on zwitterion polymer repeat units interact with each other, the question arises as to whether polyzwitterions would interact with other charged polymers. If there is no electrostatic or charge-pairing interaction between molecules, there is no driving force for intermolecular attraction and therefore no driving force for polyelectrolyte complexation, which is required for multilayer buildup.

An attempt was made to construct a multilayer from the zwitterionic polymer poly(N-propane sulfonate-2-vinyl pyridine), P2PSVP, and a negative or positive polyelectrolyte. For example, P2PSVP and PDADMA (Table I) were employed for attempted multilayer buildup at pH 5. Under this condition, the multilayer did not build because the negative sulfonate on the P2PSVP interacted with the positive pyridinium on P2PSVP, an intramolecular interaction, rather than with the PDADMA repeat unit (an intermolecular interaction). Similarly, multilayers could not be constructed from P2PSVP and PSS at near-neutral (pH5-7) conditions because the PSS does not interact sufficiently with the pyridinium nitrogen on P2PSVP. However, if the pH is lowered below about pH 2, multilayers may be built from PSS and P2PSVP. This is because at this low pH even the strongly acidic sulfonate groups on P2PSVP are protonated, leaving some of the pyridinium groups unpaired for intermolecular interactions. Multilayers constructed in this way and exposed to higher pH developed porosity and decomposed as a result of the changing internal charge within the multilayer.

Figure 12:
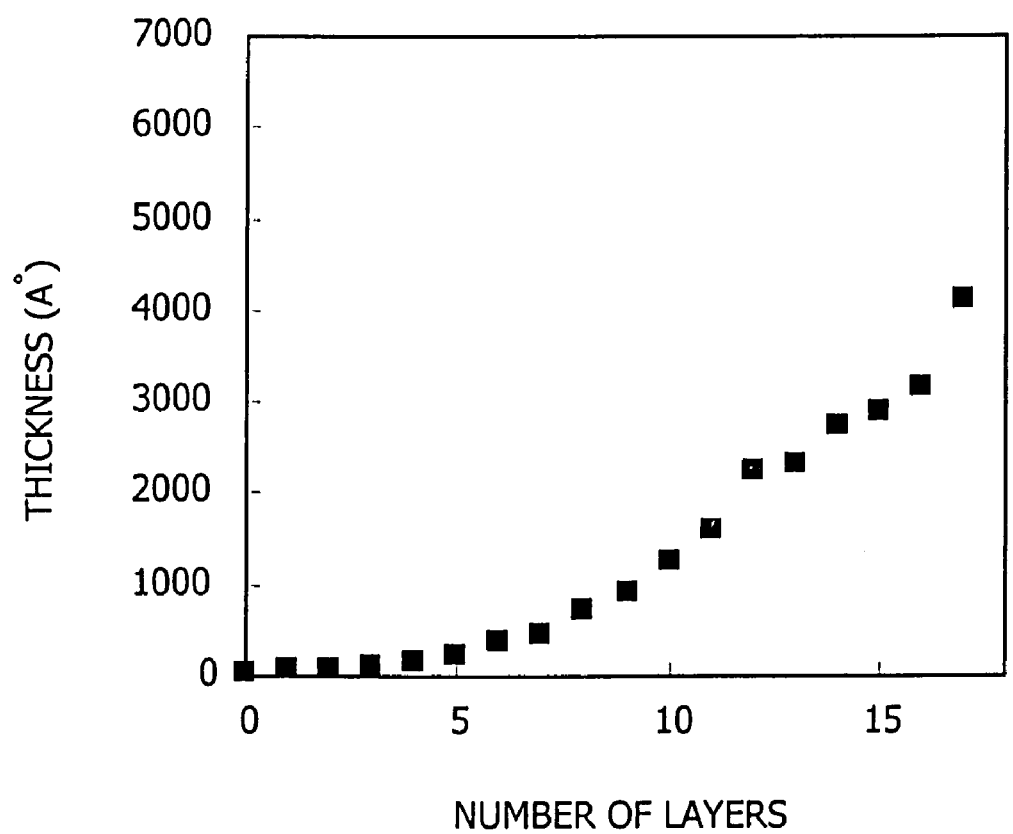
FIG. 12 is a graph of ellipsometric data showing thickness vs. number of layers for the buildup of poly(acrylic acid)-co-poly(3-[2-(acrylamido)-ethyldimethyl ammonio]propane sulfonate), PAA-co-PAEDAPS, and PAH, according to the protocol of example 8.

In another example, PAA, PDADMA and P2PSVP were employed to make a multilayer. ATR-FTIR was used to check for layer-by-layer buildup. Although ellipsometry data showed that a film grows, ATR-FTIR revealed that PDADMA displaced any P2PSVP that had weakly adsorbed to the surface—the multilayer only contained PAA and PDADMA within the bulk. Thus, it is clearly shown that polyelectrolyte bearing zwitterionic repeat units only do not form stable multilayers. By contrast, stable multilayers could be built with a copolymer comprising both zwitterion repeat units and a charged pH sensitive repeat units, such as acrylic acid, as seen in the thickness measurements in FIG. 12. FTIR revealed, in this case, the characteristic zwitterion peaks in poly(acrylic acid)-co-poly(3-[2-(acrylamido)-ethyldimethyl ammonio]propane sulfonate), PAA-co-PAEDAPS, copolymer, showed increasing quantities of zwitterion copolymer as the number of added layers increased, for a multilayer with the positive polyelectrolyte PAH. This clearly shows how the copolymer can be used in layer-by-layer buildup in contrast to the pure zwitterion polymer. The net negative charge on the zwitterion-bearing polyelectrolyte copolymer stabilizes the multilayer by providing ion pairing interaction points with oppositely charged groups on other polyelectrolyte molecules.

Example 9

Microfluidic Channels Bearing pH Sensitive Polyelectrolyte Complexes to Trap and Release Proteins The inside surface of fused silica capillary of internal diameter 50 micrometers was coated with (copolymer$_{0.2}$-blend-PDADMA$_{0.8}$/PSS)$_5$copolymer$_{0.2}$-blend-PDADMA$_{0.8}$@0.5 M NaCl @pH 2.72 system. The capillary was then rinsed with pH 7.4 buffer for an hour. A previous study showed that the surface charge polarity is negative under these conditions.

Figure 13:
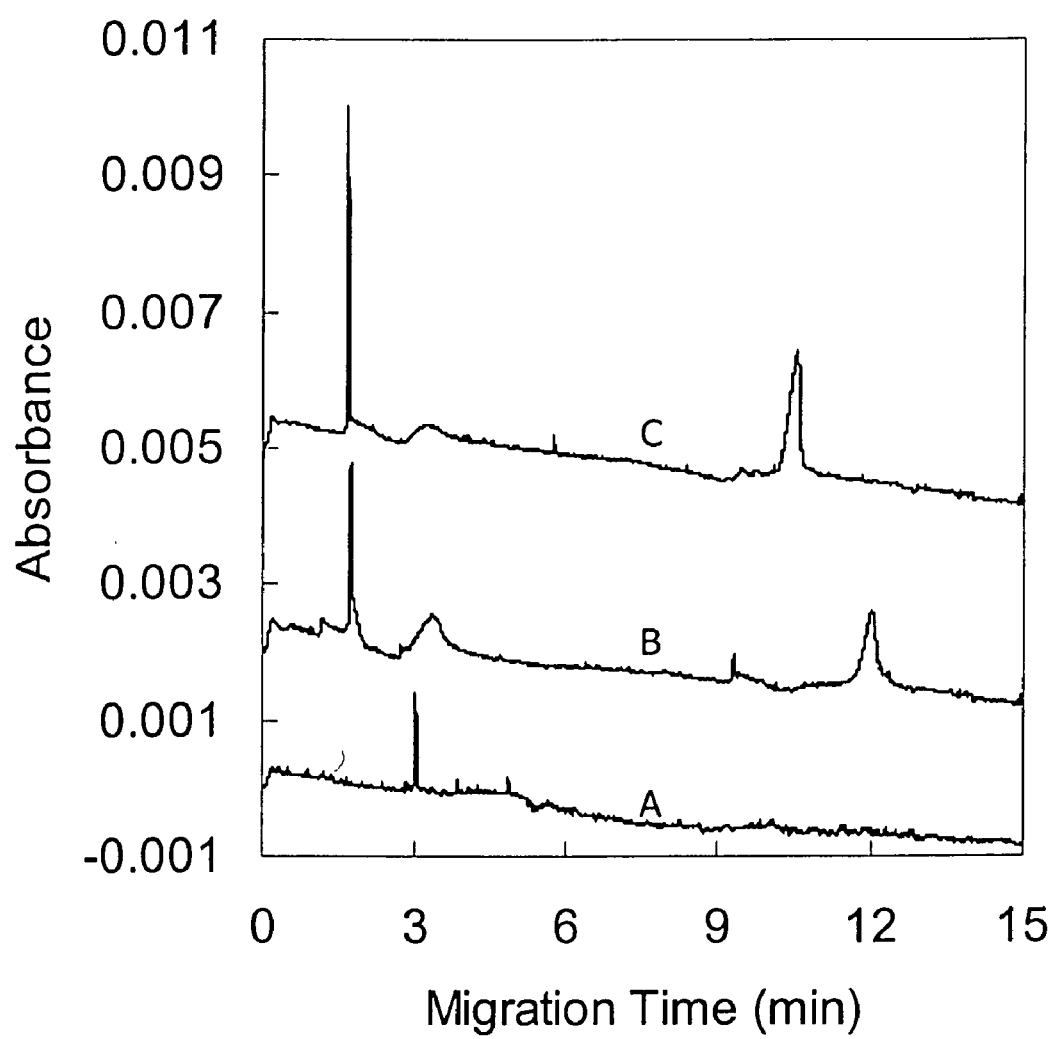
FIG. 13 shows electropherograms of protein migration acquired according to the protocol of example 9 by loading and releasing protein at different pHs on the pH-tunable PEMU coatings. (copolymer) blend/PSS)$_5$ copolymer blend @ 0.5 M NaCl @ pH 2.72 multilayer was coated on the capillary column. A: inject lysozyme sample solution (1 mg/mL, containing phenol as a neutral marker, electrokinetical, 3 kV/3 seconds) at pH 7.40. 15 kV with the normal polarity was applied. Phenol peak occurred at 3.03 minutes. No protein peak was observed. B: rinse the column with pH 2.72 buffer for 30 seconds. Inject 1 mM phenol solution. 15 kV with the reverse polarity was applied. Phenol peak occurred at 1.72 minutes. C: inject lysozyme sample solution at pH 2.72. 15 kV with the reverse polarity was applied. Phenol peak occurred at 1.67 minutes.

Separation was conducted by injecting lysozyme sample solution (1 mg/mL, containing ~1 mM phenol as a neutral marker) and then applying 15 kV with the normal polarity for 15 minutes. The phenol peak appeared at 3.03 minutes (A, FIG. 13), which further indicated the surface charge was negative. No protein peak was observed, indicating adsorption of the protein to the capillary.

To convert the surface charge polarity to positive, the capillary was rinsed with pH 2.72 buffer for 30 seconds. Phenol (1 mM) was then injected and 15 kV with the reverse polarity was applied across the column. A phenol peak appeared at 1.72 minutes (B, FIG. 13), indicating the surface charge was switched to negative. A protein peak appeared at 12.02 minutes.

Since the net surface charge polarity of the PEMU coating is opposite to that of lysozyme at pH 7.4, lysozyme is adsorbed on the coating surface and will not elute with the buffer solution. When the pH was decreased to 2.72, the surface charge of PEMU coating is altered to positive, lysozyme was released from the multilayer surface due to electrostatic repulsion and eluted as a peak.

As a comparison, lysozyme was injected at pH 2.72. 15 kV with the normal polarity was applied. A phenol peak eluted at 1.67 minutes (C, FIG. 13), which indicated that the surface charge was positive. A protein peak occurred at 10.55 minutes. The slight elution time difference between the lysozyme peak that was loaded at high pH (7.4) and released at low pH (2.72) (Curve B) and the peak by regular injection at pH 2.72 (Curve C) may be due to the kinetic effect of releasing. Experiments were repeated 5 times and the results were reproducible.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A microfluidic device for carrying a liquid, the device comprising a microfluidic channel having an interior wall and a polyelectrolyte film on the interior wall whereby liquid carried by the channel contacts the polyelectrolyte film, the polyelectrolyte film having a thickness of about 1 to about 1000 nanometers and comprising an interpenetrating network of a predominately positively charged polymer and a predominately negatively charged polymer, wherein the predominately positively charged polymer, the predominately negatively charged polymer or both is a copolymer, the copolymer comprising both (i) a pH insensitive positively or negatively charged repeat unit having a pKa greater than 9 or less than 3, and (ii) a pH sensitive repeat unit, the pH sensitive repeat unit having a pKa of 3 to 9, whereby the pH of liquid in the microfluidic channel may be used to control the velocity or direction of electroosmotic flow of the liquid within said microfluidic channel.

2. The device of claim 1 wherein the predominately positively charged polymer, the predominately negatively charged polymer or both contain pH insensitive repeat units comprising a quaternary nitrogen atom, a sulfonium atom, a phosphonium atom, a sulfonate group, a sulfate group, or a phosphate group, or combinations thereof.

3. The device of claim 1 wherein the predominately positively charged polymer, the predominately negatively charged polymer, or both contain a repeat unit derived from a (i) vinyl monomer or (ii) bifunctional condensation monomer.

4. The device of claim 3 wherein the predominately positively charged polymer, the predominately negatively charged polymer or both contain pH insensitive repeat units comprising a quaternary nitrogen atom, a sulfonium atom, a phosphonium atom, a sulfonate group, a sulfate group, or a phosphate group, or combinations thereof.

5. The device of claim 1 wherein the predominately positively charged polymer, the predominately negatively charged polymer, or both contain a repeat unit derived from a monomer selected from the group consisting of (i) a vinyl styrene sulfonic acid monomer or (ii) a bifunctional condensation monomer selected from bipyridine, diamine, dioxy, dicarboxylic acid, dicarboxylic acid chloride, and dialcohol monomers.

6. The device of claim 1 wherein the predominately positively charged polymer, the predominately negatively charged polymer or both contain pH insensitive repeat units selected from the group consisting of styrenesulfonic acid, 2-acrylamido-2-methyl-1-propane sulfonic acid, sulfonated lignin, ethylenesulfonic acid, methacryloxyethylsulfonic acid, sulfonated ether ether ketone, diallyldimethylammonium, vinylbenzyltrimethylammonium, ionenes, acryloxyethyltrimethyl ammonium chloride, methacryloxy (2-hydroxy)propyltrimethyl ammonium, N-alkylvinyl pyridiniums, N-aryl vinyl pyridinium, alkyl- or aryl imidazolium, and combinations thereof.

7. The device of claim 1 wherein the pH sensitive repeat unit contains a moiety selected from the group consisting of carboxylic acids, pyridines, imidazoles, piperidines, phosphonates, primary, secondary and tertiary amines, and combinations thereof.

8. The device of claim 1 wherein the microfluidic channel is a capillary tube having an internal diameter of about 1 to 500 micrometers.

9. The device of claim 1 wherein said channel is in a substrate selected from the group consisting of glass, silica, silicon and polymer.

10. The device of claim 1 wherein the device comprises an array of microfluidic channels.

11. The device of claim 1 wherein the film has a solution-film interface surface which contacts liquid in the microfluidic channel and a base surface contacting the interior wall and a midpoint between these surfaces wherein at least 55% of the pH sensitive units are present in the region of the film between the solution-interface surface and the midpoint.

12. The device of claim 11 wherein at least 90% of the pH sensitive units are present in the region of the film between the solution-interface surface and the midpoint.

13. The device of claim 1 wherein the film has a solution-film interface surface which contacts liquid in the microfluidic channel and at least 50% of the pH sensitive units reside in the region of the film within 10 nanometers of solution-film interface surface.

14. The device of claim 1 wherein the predominately positively charged polymer, the predominately negatively charged polymer or both contain zwitterionic repeat units.

15. The device of claim 14 wherein the film has a solution-interface surface which contacts liquid in the microfluidic channel, a base surface contacting the interior wall and a midpoint between these surfaces wherein at least 75% of the zwitterionic repeat units are present in the region of the film between the solution-interface surface and the midpoint.

16. The device of claim 15 wherein the film has a solution-film interface surface which contacts liquid in the microfluidic channel and at least 90% of the zwitterionic repeat units reside in the region of the film within 10 nanometers of solution-film interface surface.

17. The device of claim 15 wherein the zwitterionic repeat unit is 3-[2-(acrylamido)-ethyldimethyl ammonio]propane sulfonate, (AEDAPS).

18. The device of claim 1 wherein the polyelectrolyte film is crosslinked with the degree of crosslinking being between 0.1% and 10%.

19. The device of claim 1 wherein the predominately positively charged polymer, the predominately negatively charged polymer or both contain ethylene glycol repeat units.

20. A process of derivatizing the surface of a microfluidic channel, the process comprising alternately passing solutions comprising positively charged and negatively charged polyelectrolytes through the microfluidic channel to form a polyelectrolyte film on the inner surface of the channel, the film having a thickness between about 1 and about 1000 nanometers and comprising an interpenetrating network of a predominately positively charged polymer and a predominately negatively charged polymer, wherein the predominately positively charged polymer, the predominately negatively charged polymer or both is a copolymer, the copolymer comprising both (i) a pH insensitive positively or negatively charged repeat unit having a pKa greater than 9 or less than 3, and (ii) a pH sensitive repeat unit, the pH sensitive repeat unit having a pKa between 3 and 9 and complex in contact with the interior surface of a microfluidic channel whereby the pH of liquid in the microfluidic channel may be used to control the velocity or direction of electroosmotic flow of the liquid within said microfluidic channel.

21. The process of claim 20 wherein a polyelectrolyte film having a non-uniform composition is formed by the alternating exposure of said surface to solutions comprising net positive and net negative solutions of polyelectrolytes, at least one of said solutions comprising a mixture of different polyelectrolytes having the same net charge.

22. The process of claim 20 wherein the concentration of pH sensitive groups within the polyelectrolyte complex thin films is varied by diluting pH sensitive functionality with pH insensitive functionality, said dilution accomplished by mixing pH sensitive and pH insensitive polyelectrolytes, both polyelectrolytes having net negative or net positive charge, in at least one of the solutions used to deposit the polyelectrolyte complex thin film.

23. A process of controlling the flow of liquid in a microfluidic channel, the process comprising changing the pH of liquid in the microfluidic channel to change the velocity or direction of flow of the liquid in the channel, wherein the microfluidic channel has an interior wall and a polyelectrolyte film on the interior wall whereby liquid carried by the channel contacts the polyelectrolyte film, and the polyelectrolyte film has a thickness between about 1 and about 1000 nanometers and comprises an interpenetrating network of a predominately positively charged polymer and a predominately negatively charged polymer, wherein the predominately positively charged polymer, the predominately negatively charged polymer or both is a copolymer, the copolymer comprising both (i) a pH insensitive positively or negatively charged repeat unit having a pKa greater than 9 or less than 3, and (ii) a pH sensitive repeat unit, the pH sensitive repeat unit having a pKa of about 3 to 9.

24. The process of claim 23 wherein the liquid contains a polypeptide or nucleic acid having a charge and the pH of the liquid is controlled to induce the polyelectrolyte film to have a surface charge which is the same charge as that of the molecule.

25. The process of claim 23 wherein the liquid contains a polypeptide or nucleic acid having a charge and the pH of the liquid is controlled to induce the polyelectrolyte film to have a surface charge which is the opposite charge as that of the molecule.

26. The process of claim 23 wherein the liquid contains a polypeptide or nucleic acid having a charge and the pH of the liquid is controlled to cause the molecule to be sorbed by the polyelectrolyte film at a first pH and then desorbed from the polyelectrolyte film at a second pH.

27. The process of claim 26 wherein the difference between the first and second pH's is at least one pH unit.

* * * * *